(12) United States Patent
Meade Treviño et al.

(10) Patent No.: US 12,137,916 B2
(45) Date of Patent: Nov. 12, 2024

(54) DEVICE FOR OCCLUSION OF BLOOD VESSELS AND HEMORRHAGE CONTROL AND METHOD FOR ITS PLACEMENT AND REMOVAL

(71) Applicant: VIRETEC GESTION Y DESARROLLO, S.A. DE C.V., San Luis Potosí (MX)

(72) Inventors: Paulo Felipe Meade Treviño, Soledad De Graciano Sánchez (MX); Adriana Gatica Díaz Escobar, Mexico City (MX); Bogar Israel Patiño Roa, Mexico City (MX); Karina Alin Quintero Tapia, Estado de México (MX); Emilio Sacristán Rock, Mexico City (MX)

(73) Assignee: VIRETEC GESTION Y DESARROLLO, S.A. DE C.V., San Luis Potosí (MX)

( * ) Notice: Subject to any disclaimer, the term of this patent is extended or adjusted under 35 U.S.C. 154(b) by 821 days.

(21) Appl. No.: 17/256,895

(22) PCT Filed: Jun. 27, 2019

(86) PCT No.: PCT/IB2019/055476
§ 371 (c)(1),
(2) Date: Dec. 29, 2020

(87) PCT Pub. No.: WO2020/003214
PCT Pub. Date: Jan. 2, 2020

(65) Prior Publication Data
US 2021/0282782 A1   Sep. 16, 2021

(30) Foreign Application Priority Data

Jun. 29, 2018   (MX) .................. MX/a/2018/008202

(51) Int. Cl.
*A61B 17/122*   (2006.01)
*A61B 17/128*   (2006.01)
*A61B 17/00*   (2006.01)

(52) U.S. Cl.
CPC .......... *A61B 17/122* (2013.01); *A61B 17/128* (2013.01); *A61B 2017/00367* (2013.01)

(58) Field of Classification Search
CPC ................ A61B 17/122; A61B 17/128; A61B 2017/00367; A61B 17/0487; A61B 17/12;
(Continued)

(56) References Cited

U.S. PATENT DOCUMENTS 3,509,882 A * 5/1970 Blake .................. A61B 17/1227
24/529
3,510,923 A * 5/1970 Blake .................. A61B 17/0206
269/286

(Continued)

*Primary Examiner* — Sarah A Long
*Assistant Examiner* — James R McGinnity
(74) *Attorney, Agent, or Firm* — Michael D. Eisenberg

(57) ABSTRACT

A device for occlusion of blood vessels and hemorrhage control, whose design it allows to control the force of application of the blood vessel that is intended to be occluded and during its placement, applies always the same force, regardless of the diameter of the blood vessel to be occluded and/or the dimensions of the tissue that surrounds it.

11 Claims, 40 Drawing Sheets

(58) Field of Classification Search
CPC ...... A61B 17/1227; A61B 2017/00371; A61B 2017/00384; A61B 2017/081; A61B 2017/12004; A61F 6/20; A61F 6/202; A61F 6/206; A61F 6/208; B25B 5/00; B25B 5/02; B25B 5/068; B25B 5/085; B25B 5/102; B25B 5/127
See application file for complete search history.

(56) References Cited

U.S. PATENT DOCUMENTS

| | | | | |
|---|---|---|---|---|
| 4,817,604 | A * | 4/1989 | Smith, III | A61B 17/1227 606/151 |
| 4,931,058 | A * | 6/1990 | Cooper | A61B 17/1227 24/523 |
| 5,653,720 | A * | 8/1997 | Johnson | A61B 17/1227 606/151 |
| 6,159,207 | A * | 12/2000 | Yoon | A61B 90/04 606/41 |
| 6,267,773 | B1 * | 7/2001 | Gadberry | A61B 17/1227 606/151 |
| 9,427,245 | B1 * | 8/2016 | Biolchini, Jr. | A61B 17/2833 |
| 2003/0176879 | A1 * | 9/2003 | Anderson | A61B 17/1227 606/151 |
| 2004/0143276 | A1 * | 7/2004 | Sturtz | A61B 17/1227 606/151 |
| 2005/0222590 | A1 * | 10/2005 | Gadberry | A61B 17/1227 606/151 |
| 2014/0243862 | A1 * | 8/2014 | Bagaoisan | A61B 17/122 606/157 |
| 2016/0258183 | A1 * | 9/2016 | Masserant | E04H 17/161 |
| 2017/0209022 | A1 * | 7/2017 | Molnar | A61M 16/0465 |

* cited by examiner

DEVICE FOR OCCLUSION OF BLOOD VESSELS AND HEMORRHAGE CONTROL AND METHOD FOR ITS PLACEMENT AND REMOVAL

FIELD OF THE INVENTION

This invention pertains to the principles and techniques used in biomedical engineering for their design, manufacture and functioning of medical devices specifically clips, clamps and devices for vascular occlusion, and particularly, this invention pertains to a device for occlusion and control of the obstetrics hemorrhage by temporary compression of the uterine blood vessels.

Likewise, this invention pertains to the method for the obstruction of vaginal uterine arteries, using the device presented in this document.

BACKGROUND DISCLOSURE

Hemorrhage is the flow of blood that occurs outside of the natural blood circulation, which may consist of a light bleeding caused by a slight wound, or else, it may consist of a great loss of blood having severe consequences for functioning and/or life. In consequence, hemorrhage, is the exit of blood out of blood vessels, due to the lack of continuity in them.

In the case of external hemorrhages, the main measure to take is to apply direct pressure to inhibit bleeding repairing or tying afterwards.

The use of tourniquets is recommended for massive hemorrhages, in view of the danger of necrosis of the bleeding limb.

According to the Spanish Society of Gynecology and Obstetrics (Sociedad Española de Ginecología y Obstetricia), postpartum hemorrhage represents the loss of more than 500 ml of blood from the genital tract and more than 1000 ml of blood after a cesarean section. Postpartum hemorrhage is the main cause of perinatal maternal morbidity in developed nations and one cause of morbidity is developing nations.

According to WHO, postpartum hemorrhage PPH is defined as the loss of blood (500 ml or more) within 24 hours of delivery. Postpartum hemorrhage is one of the main causes of perinatal maternal morbidity globally. It is estimated that it happens to 11% of women who give birth to a live baby. The incidence is much higher in developing nations, where a great majority of women do not have the possibility of giving birth attended by trained personnel.

Around 14 million women suffer from severe blood loss after childbirth and 1% of these die as a consequence. An additional 12% survives with severe anemia (World Health Organization, 2015).

The two main causes of maternal death in Mexico are: Maternal Hypertensive Disorder, which accounts for 25% of maternal deaths, and obstetric hemorrhage which accounts for 19.6% of the total, among which are women who die of placenta praevia with hemorrhage, premature detachment of placenta, hemorrhage of the third period of labor and immediate and late bleedings (CONEVAL 2010).

According to the Maternal Mortality Observatory in Mexico (Observatorio de Mortalidad Materna en Mexico), the total maternal deaths in our country during 2013 was 861, not considering those as a result of carcinoma or those that occurred after 42 days from childbirth, which means indirect or delayed. Out of the total maternal deaths, is estimated that 17.5% (150 deaths) were caused by hemorrhage of pregnancy, childbirth and puerperium (Observatorio de Mortalidad Materna en México, 2013).

There are several occlusion mechanisms for the interruption of blood flow, which can be classified as temporary or definite, according to its permanence; as complete or partial, according to its degree of occlusion; and finally, it can be classified as chemical, mechanical, by ionizing and thermal radiation, according to the means used for occlusion of blood flow.

In this context, biomedical engineering has been dedicated to designing, developing and construction of devices, clamps, clips, etc. with the purpose of interrupting blood flow, to avoid massive hemorrhage and consequently, the patient's death.

Therefore, in the state-of-the-art there are several and diverse orthotic devices, which is the case of U.S. Pat. No. 3,509,882 which is part of the public domain, consisting of a spring clamp for fastening which include one pair of parallel grips with a soft compressible surface. The mechanism of opening and compression described above, is based on a cylinder, a piston and a compression spring that extends through both.

On the other hand, U.S. Pat. No. 5,800,561, describes a device and method for the control of hemorrhages in intestines, arteries, veins and other organs, limiting the applied pressure between 100 and 300 mmHG.

Some patents percent various solutions, such as an instrument for placing the clip through a small incision, as reported on U.S. Pat. No. 5,921,997; one clip for the occlusion of the uterine arteries with a pair of "legs" joined together with pivot point protected by document U.S. Pat. No. 4,671,281; and the development of U.S. Pat. No. 4,458,682 which claims one clip for the occlusion of uterine arteries, with a pair of legs that allow for the parallel occlusion of the uterine arteries and fastening of the clip through a ring.

Also found in the state-of-the-art, is U.S. Pat. No. 4,931,058, pertaining to spring clamps with parallel grips. One clip with improved parallel jaw spring which includes (a) and elongated support made of elastic polymeric material, this support has: a generally cylindrical lateral wall; one elongated conduit that extends longitudinally, closed on one end; one fixed grip element that extends radially from the lateral wall adjacent to that and; lateral opening grooves diametrically aligned through such lateral wall, one of such grooves has closed ends and is located intermediately between the lid on the jaw element; (b) a second telescopically elongated support which is received inside the conduit of the first support for longitudinal movement with respect to itself, the supports are preferably cylindrical adjusting through a telescopic coupling; a second fixed grip element which extends radially from one end of the second support to the other, allowing the displacement of the second jaw element towards the first jaw element, as a result of the longitudinal movement of the cylindrical supports. Additionally, the clamps have elastic media to push the first and second support for the telescopic movement, one against the other, so that both grips apply pressure.

In the prior art there is also U.S. Pat. No. 6,802,848 which describes clamps that include a first grip that has a first body element and a second grip that has a second body element, both body elements are in a telescopic relationship able to zoom the grips in and out, sliding along one longitudinal axis defined by the first and second body elements. Such displacement is capable of fixation in order to define the pressure of the clamp grips in two or more positions along the axis by means of notches that extend from guide grooves or attachable cam pins or separated indentations.

International Publication Number WO 2006/019969, refers to an intravaginal staple to occlude the uterine artery of the patient under treatment for uterine disorder such as postpartum uterine bleeding by cesarean or similar. The intravaginal staple includes an occlusion spindle that has a superficial pressure application and at least one, preferably two legs of tissue penetration which are endowed with bumps that help maintain the staple legs inside the penetrated tissue. At least part of the staple is preferably formed of bioabsorbable material. The system of staple display may be endowed with elongated handles and staple implementation mechanisms at the distal ends of the handles to push the legs of the staples in the tissue bundle over the uterine artery for the apply pressure by the occlusion spindle to occlude the uterine artery.

Also available is International Publication Number WO 2002/078522B1 which reports a system for compression of one or both uterine arteries of the patient, that has a form such that it allows for one self-positioning. One or more Doppler chips may be mounted or incorporated in the system for an improved identification of the uterine artery as well as supervision of the blood flow in it. An element of the tentacle type may additionally be included in order to fix the system to the cervix of the patient.

In International Publication Number WO 2004/045420 are found devices, systems and methods to reduce or temporarily suppress blood flow by including blood vessels. One such device for artery occlusion that includes an application element of pressure deployment with a location sensor, and an applicator. The location center is configured to detect a blood vessel, that can be occluded by compression by such element of pressure. The invention can be used in the treatment of disorders and illnesses that can be treated by uterine artery occlusion, such as uterine fibroma, dysfunctional uterine hemorrhage, postpartum hemorrhage and uterine bleeding associated to cesarean section.

Besides the above explanations for the state-of-the-art associated to this invention, and for the specific marketing case, the following companies can be considered: Scanlan International, a Swiss company that manufactures medical equipment founded in 1921 and Edwards Lifesciences, an American company founded in 1958, a leader in the development of technologies for the treatment of structural cardiac illnesses and monitoring of intensive care. The products manufactured and commercialized by these companies consist of temporary atraumatic occlusion instruments in the form of clips and clamps manufactured in different materials. They can be disposable or reusable and are offered in different sizes from 4 to 86 mm.

In the background of this subject, it is possible to find devices which, besides occlusion functions, allow the application of consistent tension; minimization of vascular damage due to soft paddles; sustain a combination of resilience and traction and, the application of the necessary pressure degree thanks to the dented structure of the clamps, such as the atraumatic vascular occlusion clamps can offer for different vascular structures, which are commercialized by Edward Lifesciences under the Fogarty® brand, as well as temporary occlusion clips under the Heifetz® brand, capable of light pressure application.

Among the products for vascular occlusion identified in the market, are those that are manufactured for Scanlan international and commercialized under the Yasarig® brand which are reusable clips, flat or curved for temporary vascular occlusion; and Vascu-Satt® which are plastic ultralight disposable clips for temporary vascular occlusion of different forms and sizes to apply different pressures.

According to the above explanations, it can be seen that there is a wide variety of devices found in the state-of-the-art some of which are here discussed, which were designed and developed for the occlusion functions, allow the application of pressure trying to minimize the vascular damage that such pressure can cause. Nevertheless, all of them present certain disadvantages, among which we can mention that the devices, clamps or clips used for the occlusion of arteries, regulate the applied force by means of extension springs, compression or twisting, preventing the exercise of an independent force from the anatomic dimensions of the occluded zone; likewise, for the state-of-the-art devices, there will always be a different force to be applied taking into account the zone, the diameter of the vessel to be occluded and the dimensions of the surrounding tissue.

As a consequence of the above, it has been attempted to suppress the inconveniences presented by the methods, systems, and blood vessel occlusion devices of the prior art, by developing a new device for the occlusion of blood vessels and hemorrhage control, that has been endowed with a deformable polymeric piece, which at the same time it allows for the control of the occlusion force on the blood vessel in question (without hurting the tissue of the zone to be occluded), avoids the use of elastic media, deformable and/or generally metallic compression instruments, in such a way that when placing the occlusion device of this invention, it will function efficiently, always applying the same force, regardless of the diameter of the blood vessel, veins or arteries, as well as the dimensions of the surrounding tissue.

Another important aspect of the invention presented in this document, is to provide an ergonomic and safe occlusion device capable of being applied to a patient by means of Foerster clamps.

PURPOSE OF THE INVENTION

Taking into account the defects encountered in the state-of-the-art, the main purpose of this invention is to provide a device for the occlusion of blood vessels and hemorrhage control, whose design and construction is extremely simple and economic, while being highly efficient, practical and functional.

In view of the versatility of the invention presented in this document, several purposes stand out, among them its placement and removal method, as well as others described in the subsequent paragraphs.

To provide a device for the occlusion of blood vessels and hemorrhage control, whose design and configuration elements allow for the control the force applied on the blood vessel in question.

To provide a device for the occlusion of blood vessels and hemorrhage control, that consistently requires the same force for its placement regardless of the diameter of the blood vessel being occluded and the dimensions of the surrounding tissue.

To provide a device for the occlusion of blood vessels and hemorrhage control, whose ergonomic design allows for placement and removal from the patient by means of Foerster clamps.

To provide a device for the occlusion of blood vessels and hemorrhage control, which can be placed on the blood vessels on the right, as well as the left side of the body of the patient that requires it and which can be easily placed by right-handed and left-handed personnel.

To provide a device for the occlusion of blood vessels and hemorrhage control that efficiently complies with the occlusion function of the blood vessel where it is applied, without hurting or affecting the tissue of the occlusion area.

To provide a device for occlusion of blood vessels and hemorrhage control, which prevents the risk of tissue hypoxia and/or necrosis on the area where it is placed.

To provide a device for occlusion of blood vessels and hemorrhage control, which because of its design and the deformable polymeric piece with which it's been endowed, allows for control of the force of occlusion in the blood vessel where it is applied, without hurting the tissue around the occlusion area.

Likewise, another main purpose for the invention is to describe a method for the placement and removal of the device presented in this document.

BRIEF DESCRIPTION OF THE FIGURES

The novelty aspects that are considered characteristic in the present invention, will be established in detail in the annexed patent claims; nevertheless, the invention itself, due to its structural organization as much as other objects and advantages, will be better understood in the following detailed description of certain preferred modalities when they are read in relation to the drawings that are included, where:

DETAIL DESCRIPTION OF THE INVENTION

Figure 1:
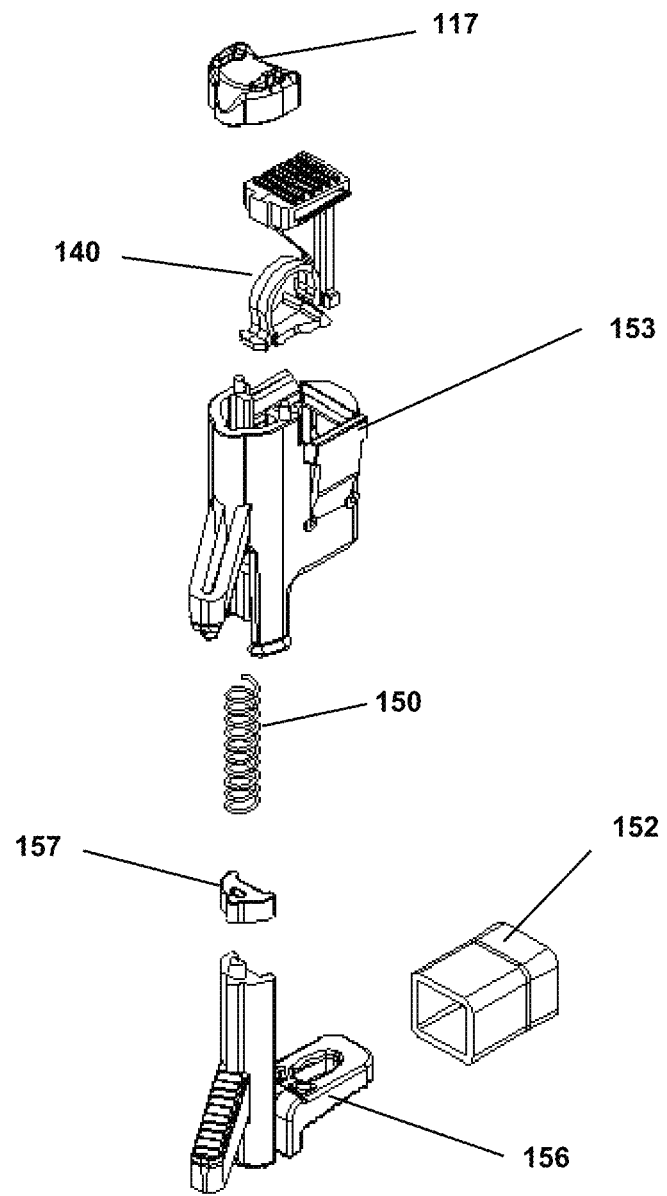
FIG. 1 is an exploded view drawing of the frontal perspective of the device for occlusion of blood vessels and hemorrhage control of the invention, whose parts have been designed pursuant to the principles of a particularly preferred modality.

A specifically preferred materialization of the invention will be henceforth described with the drawings attached, where:

The device for occlusion of blood vessels 100 object of the invention, consists of an upper assembly housing 110; a lower assembly housing 120, and; a suspension system made up of a deformable element 140 and elastic means 150.

Figure 3:
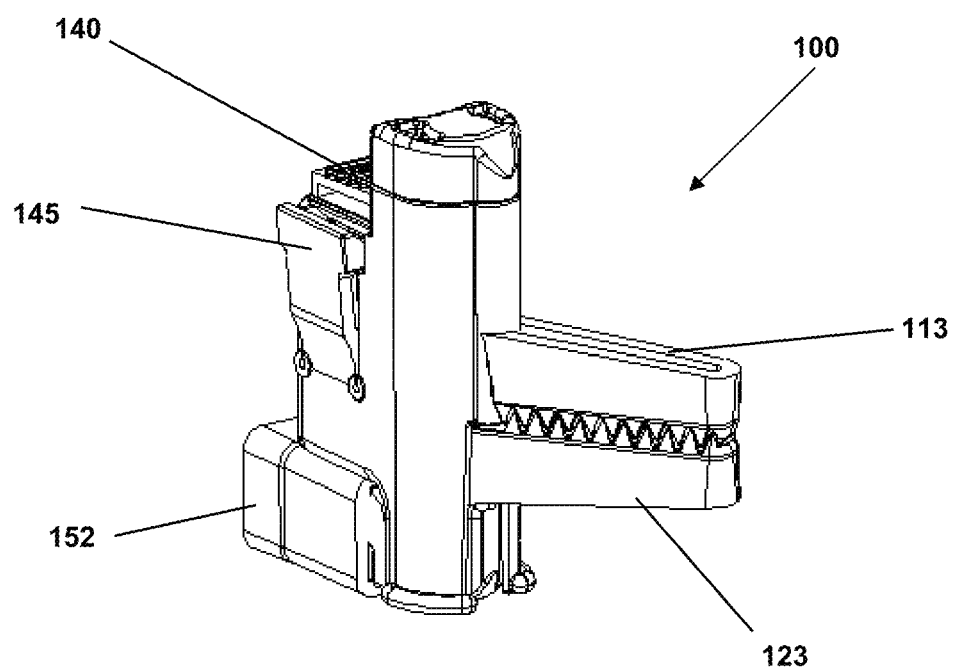
FIG. 3, is a view in perspective of the frontal plane of the device of this invention showing the assembly in a closed position.
Figure 7:
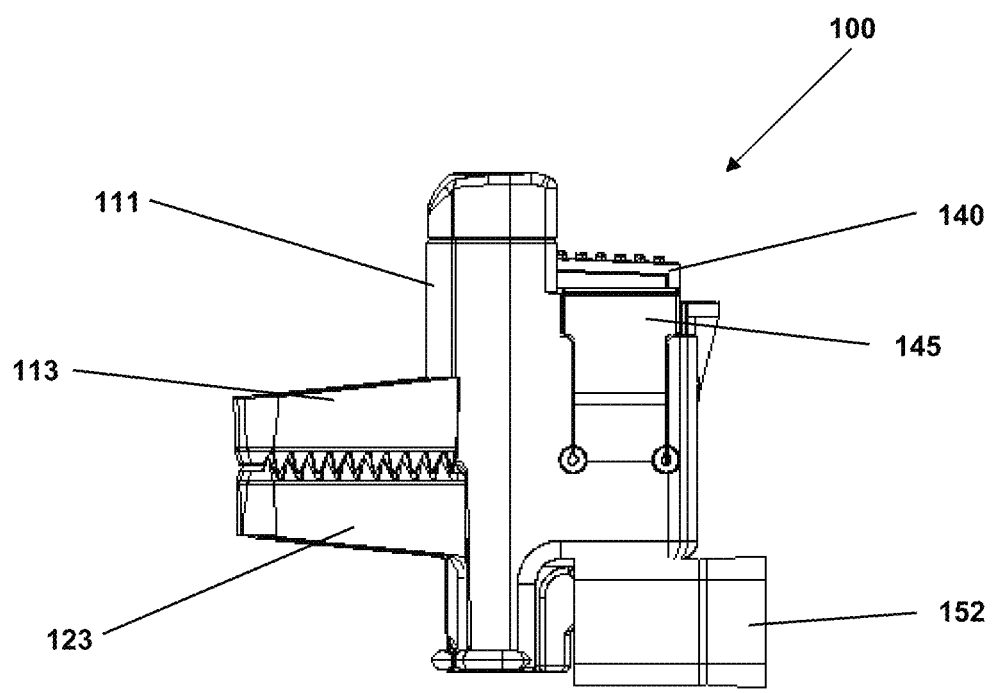
FIG. 7, is a right lateral view of the device shown in FIG. 3.

In FIGS. 3 and 7, which are described further down, the device of this invention is shown in a closed position.

Figure 10:
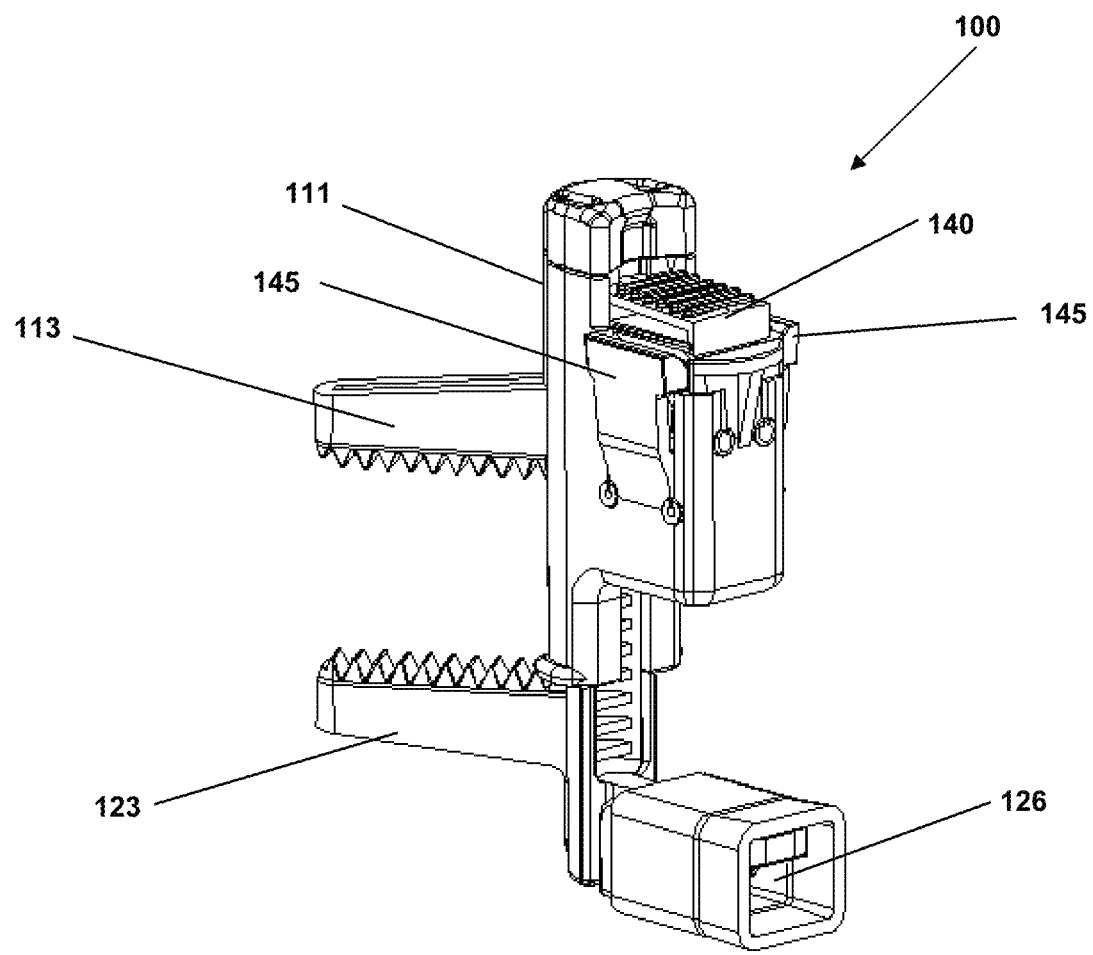
FIG. 10, is a rear right lateral view of the device shown in FIG. 3, showing the assembled device in an open position.
Figure 11:
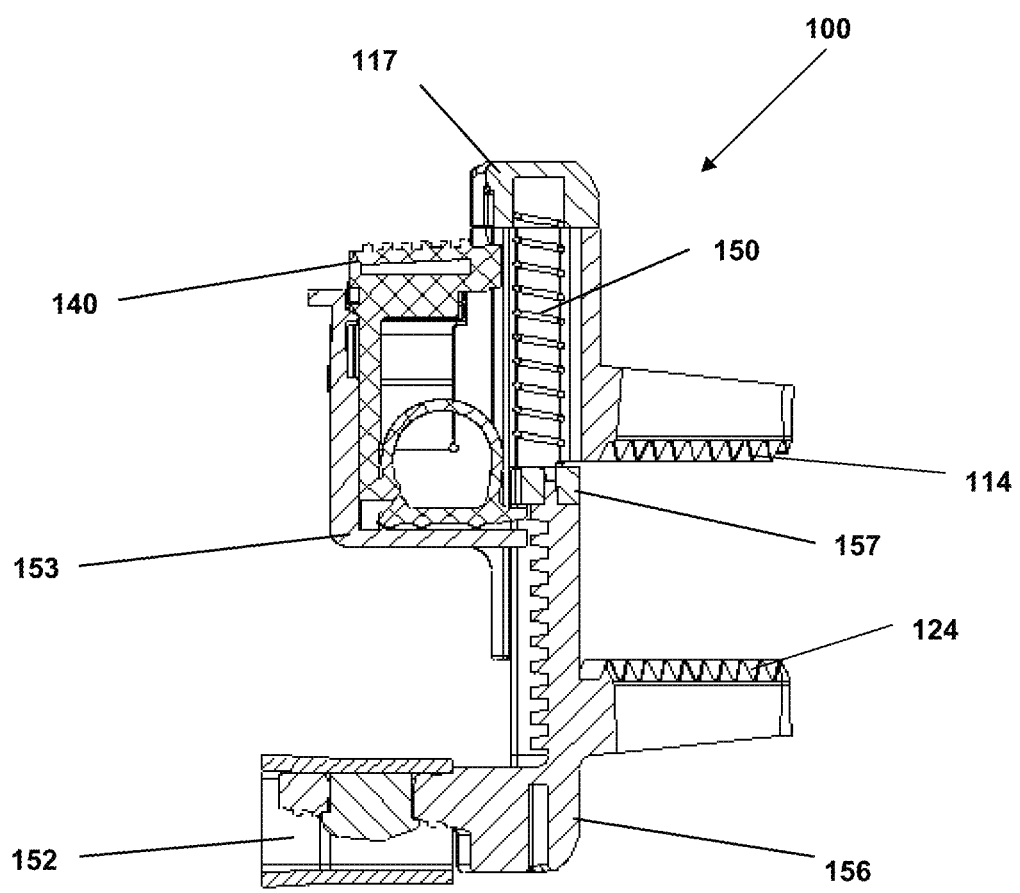
FIG. 11, is a view of the cross-section of the left plane of the device shown in Figure three, showing the assembled device in an open position.

In FIGS. 10 and 11, which are described further down, the device of this invention is shown in an open position.

FIG. 1, is an exploded view of the perspective of the frontal plane of the device for the occlusion of blood vessels and hemorrhage control, the object of this invention, whose pieces have been designed and are described according to the principles of a particularly preferred modality, the top lid stands out 117, the deformable element 140, the top carcass 153; the elastic medias 150; the bottom carcass 157; the flexible grip piece 152; and the bottom carcass 156.

Figure 2:
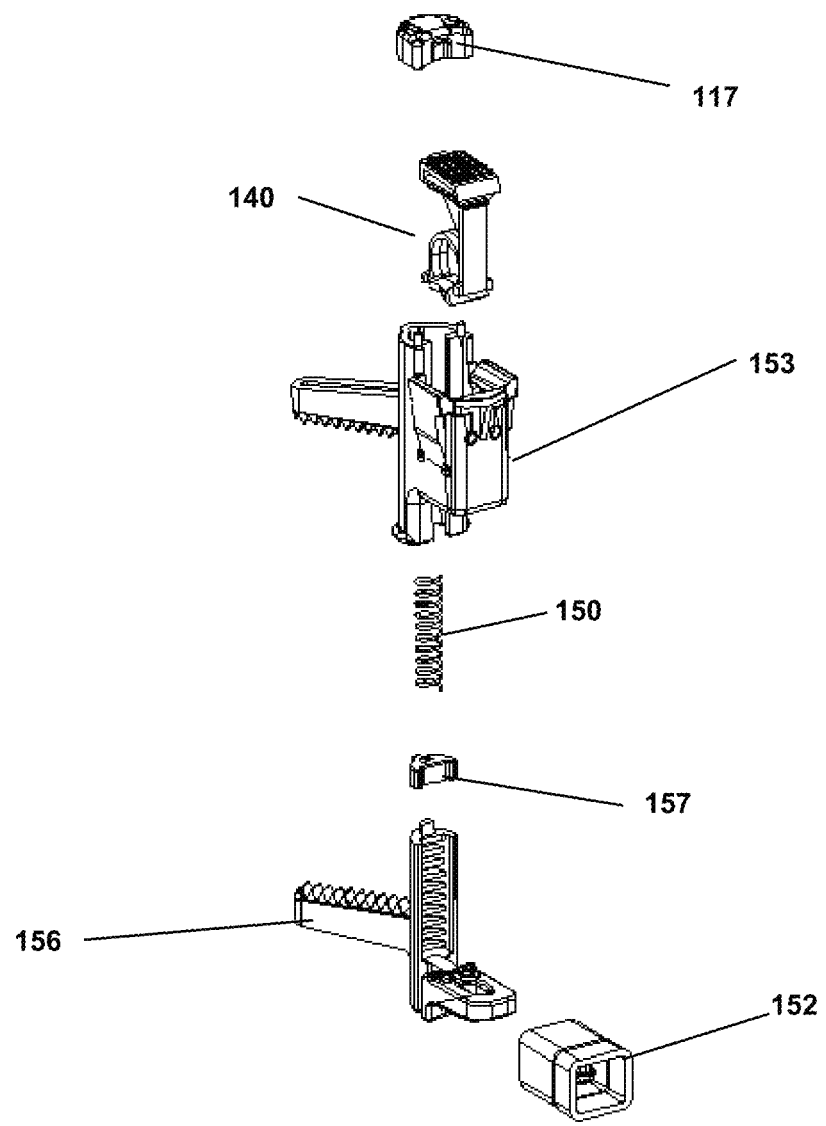
FIG. 2, is an exploded view of the rear plane perspective of the device for occlusion of blood vessels and hemorrhage control shown in FIG. 1.

FIG. 2, is a view of the perspective of the rear plane of the device shown in FIG. 1, where of the top lid stands out 117, the deformable element 140, the top carcass 153; the elastic media 150; the bottom carcass lid 157; the flexible grip part 152, and the bottom carcass FIG. 3, shows a frontal plane perspective of the device 100, in a closed position, where the pressure paddle stands out 113, formed in one piece in the top assembly carcass 110; the lower pressure paddle 123, formed in one piece in the bottom assembly carcass 120; the flexible grip part 152; the end of the pressure release button 145, the deformable element 140.

Figure 4:
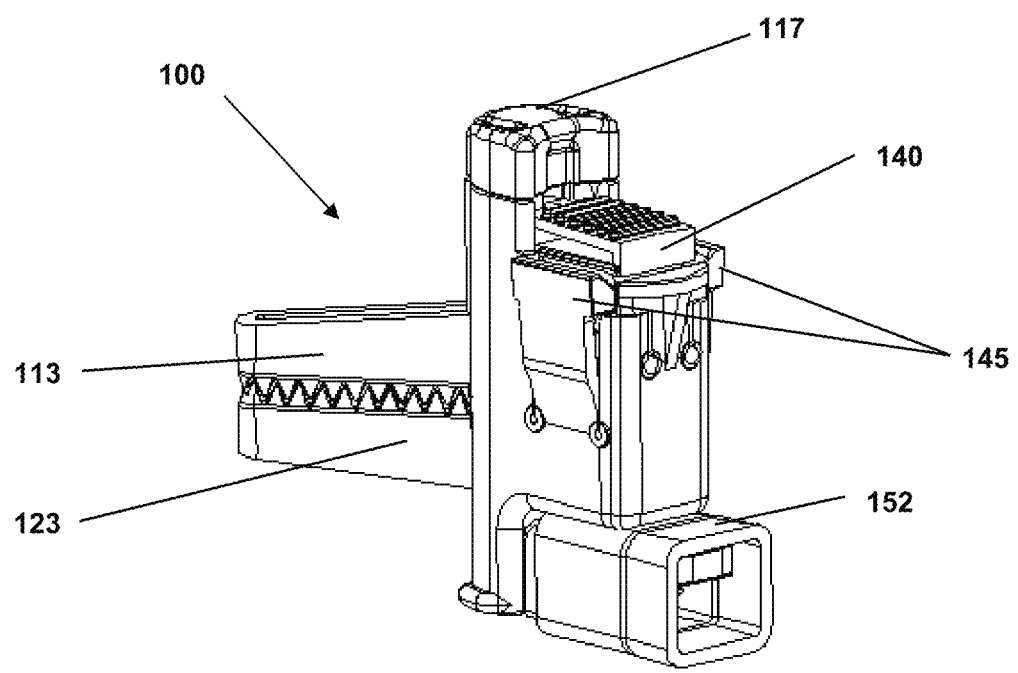
FIG. 4, is a view in perspective of the rear plane of the device shown in FIG. 3.

FIG. 4, shows a perspective view of the rear plane of the device 100, where the top lid 117 can be seen, the deformable element 140; the ends of the pressure release button 145; the flexible grip part 152; the lower pressure paddle 123, and; the top pressure paddle 113.

Figure 5:
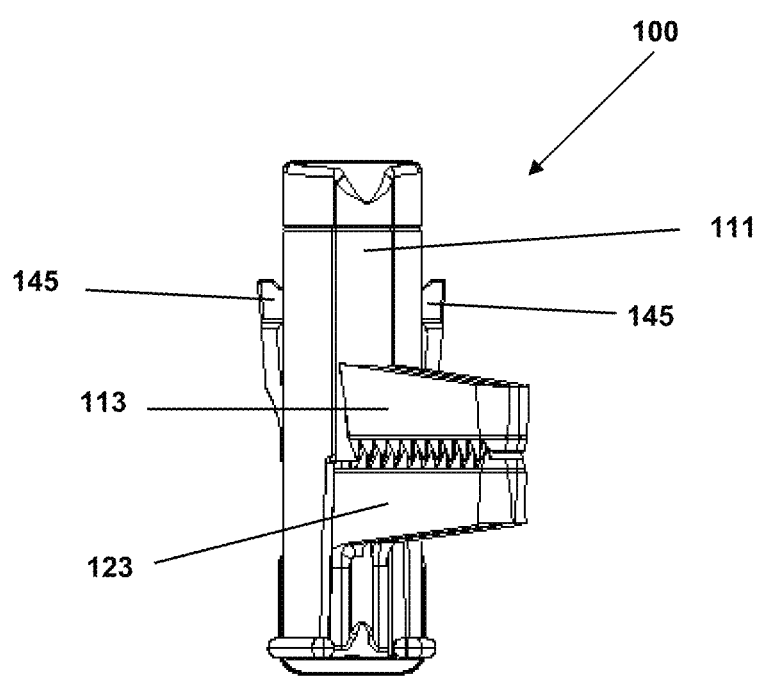
FIG. 5, is a view of the frontal plane of the device shown in FIG. 3.

FIG. 5, is a view of the frontal plane of the device 100, in which the semi cylindrical wall can be seen 111, molded in the frontal part of the frontal top assembly carcass 110, the ends of release button 145; the lower pressure paddle 123, and; the top pressure paddle 113.

Figure 6:
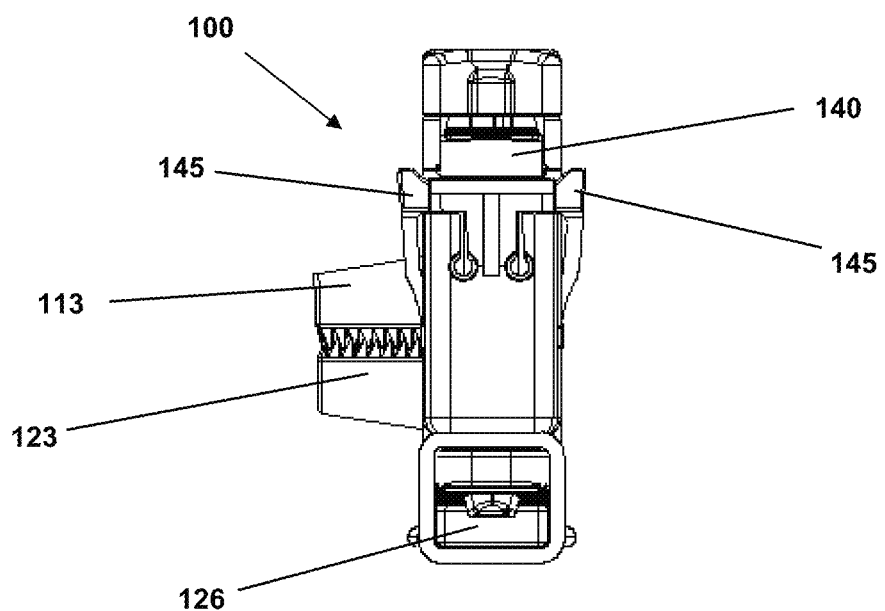
FIG. 6, is a view of the rear plane of the device shown in FIG. 3.

FIG. 6, is a view of the rear plane of the device 100, in which the top part of the deformable element 140 can be seen; the ends of release button 145, the rear window 126 of the bottom assembly 120; the bottom pressure paddle 123, and; the top pressure paddle 113.

FIG. 7, is a right lateral view of the device 100, in which can be seen the top part—the deformable element 140; one end of the release button 145; the flexible grip piece 152; the lower pressure paddle 123, formed in one piece in the bottom assembly carcass 120; the lower pressure paddle 113, formed in one piece in the frontal top assembly carcass 110, and; the semi cylindrical wall 111, molded in the frontal part of the frontal top assembly carcass 110.

Figure 8:
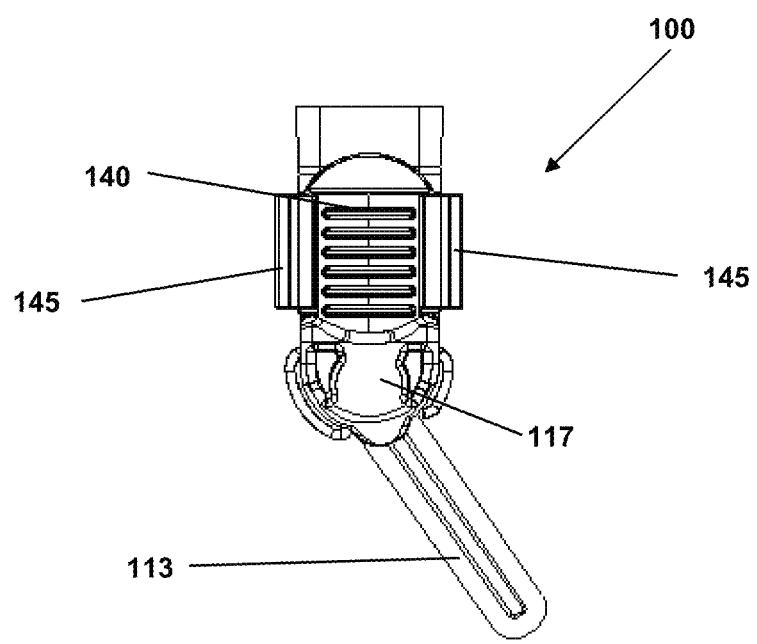
FIG. 8, is a view of the top plane of the device shown in FIG. 3.

FIG. 8, is a view of the top plane of the device 100, in which the top part of the deformable element 140; the top part of the ends of the release buttons 145; the top lid 117 and; the top pressure paddle 113, formed in one piece in the frontal carcass of the top assembly 110.

Taking the view of the top plane of the device into account 100, in a particularly preferred modality of this invention, the top pressure paddle 113, shows an angle of approximately 55° towards the right in relation to the center of the top assembly carcass 110.

Figure 9:
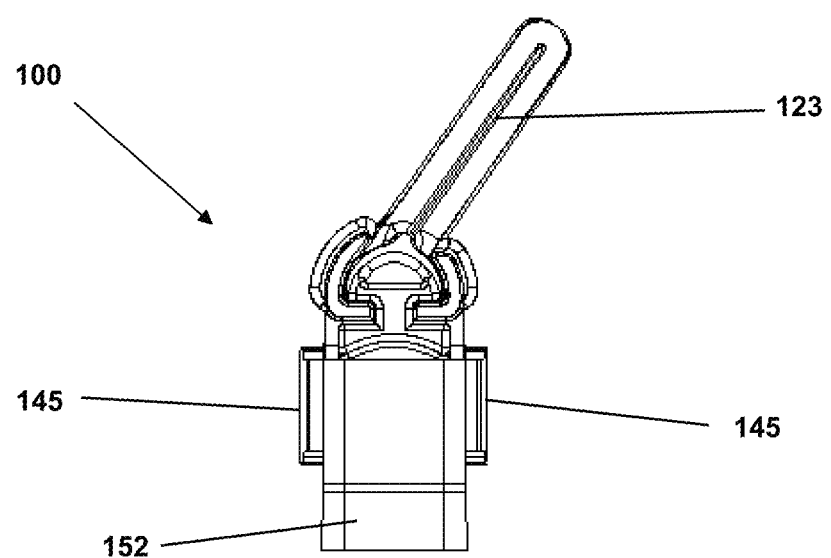
FIG. 9, is a view of the bottom plane of the device shown in FIG. 3.

FIG. 9, is a view of the bottom plane of the device 100, in which the bottom pressure paddle 123 can be seen, formed in one piece in the bottom frontal carcass assembly 120; the ends of pressure release buttons 145, and; the flexible grip piece 152.

Taking the view of the bottom plane of the device into account 100, in a particularly preferred modality of this invention, the lower pressure paddle 123, shows an angle of approximately 55° towards the right in relation to the top frontal assembly carcass 110.

FIG. 10, is a right lateral view of the device 100, shown in an open position, in which stands out the top part of the deformable element 140; the ends pressure release buttons 145; the posterior window 126 of the bottom assembly 120; the bottom pressure paddle 123, formed in one piece in the bottom frontal assembly carcass 120; the top pressure paddle 113, formed in one piece in the top assembly carcass 110, and the semi cylindrical frontal wall 111, molded in the frontal part of the frontal top assembly piece 110.

Figure 12:
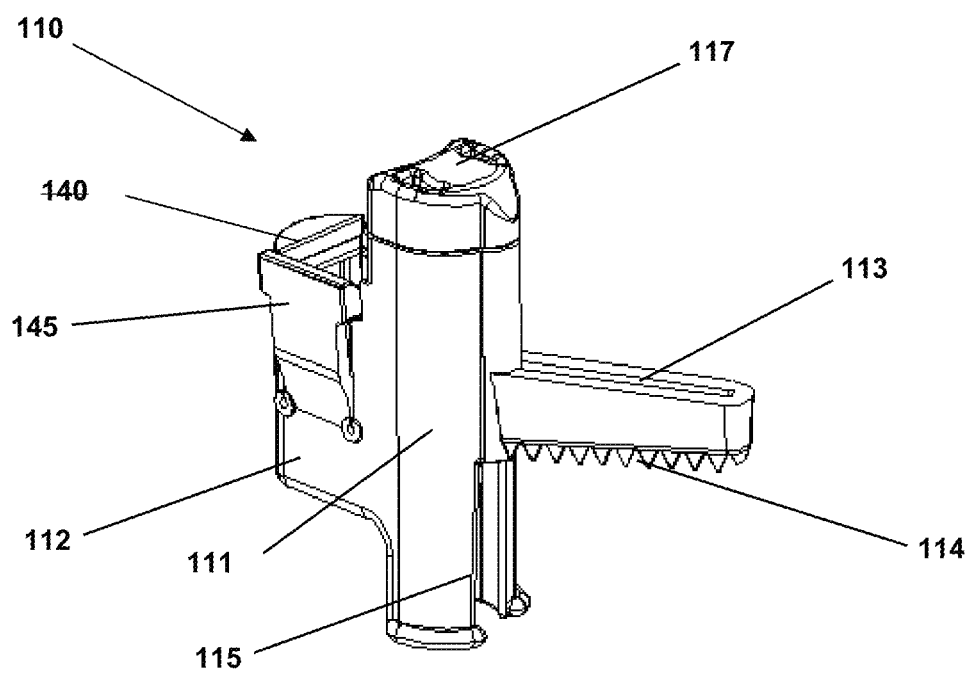
FIG. 12, is a view of the frontal perspective of the top front assembly carcass shown in FIG. 1.
Figure 19:
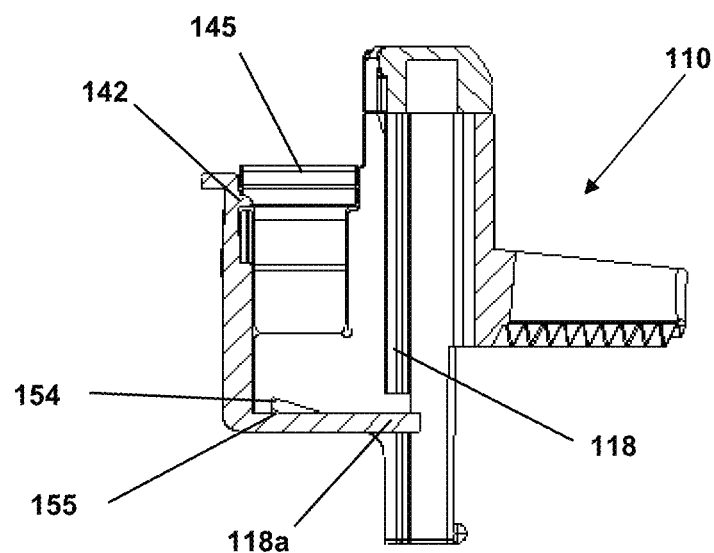
FIG. 19, is a view of the left side in cross-section of the carcass of the top assembly shown in FIG. 12.

The frontal carcass of the top assembly 110, which will be shown further on when describing FIGS. 12 and 19, covers one semi cylindrical frontal wall 111; one top pressure paddle 113, which extends radially and at a 90° angle from the center of the semi cylindrical frontal wall 111, which have been molded in one piece in the frontal top assembly carcass 110. Such pressure paddle 113, includes a number of retention media on its bottom surface 114 uniformly distributed, which in a preferred modality of this invention, consists of superficial slots (dented), that extend equidistant from each other and in the whole bottom area of said pressure paddle 113.

FIG. 11, is a cross-section view of the left plane of the device 100, in which the elastic media 150 stands out; the retention media 114 of the top pressure paddle 113; the lid of the bottom carcass 157; the retention media 124 of the bottom pressure paddle 123; the bottom carcass 156, molded in one piece; the flexible grip piece 152; the top carcass 153, molded in one piece, and; the deformable element 140, the top lid 117.

FIG. 12, is a view of the frontal perspective of the frontal carcass of the top assembly 110 of the device 100, in which of the top lid 117 stands out, the top pressure paddle 113, formed in one piece in the frontal top assembly carcass 110; the dented retention media 114, which had been molded on the top pressure paddle 113, the window 115; the semi-cylindrical front wall 111, molded into the front of the upper assembly front housing 110; the side wall 112 molded into the upper housing, and; the pressure release button 145.

The semi cylindrical frontal wall 111, includes a window 115, formed by an opening, preferably rectangular, which extends from the lower surface of the top pressure paddle 113, to the lower limit of said semi cylindrical frontal wall 111.

The width of the window 115, is slightly larger than the width of the joint of the pressure paddle 113, thus allowing that the semi cylindrical frontal wall 111, extends downwards over the sides of the window 115, delimiting in this way the opening of the window 115.

Figure 13:
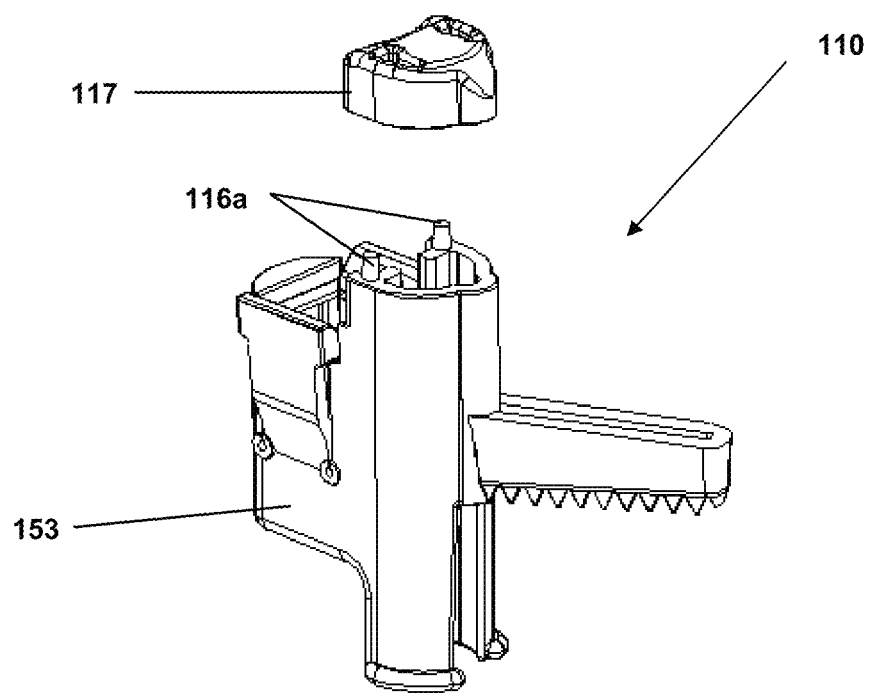
FIG. 13, is an exploded view of the frontal perspective of the top front carcass of the assembly of the device shown in FIG. 1.

FIG. 13, is an exploded view of frontal perspective of the top assembly carcass 110 of the device 100, in which the top lid 117, stands out, the top carcass 153, and; the clamping assembly means 116a.

Figure 14:
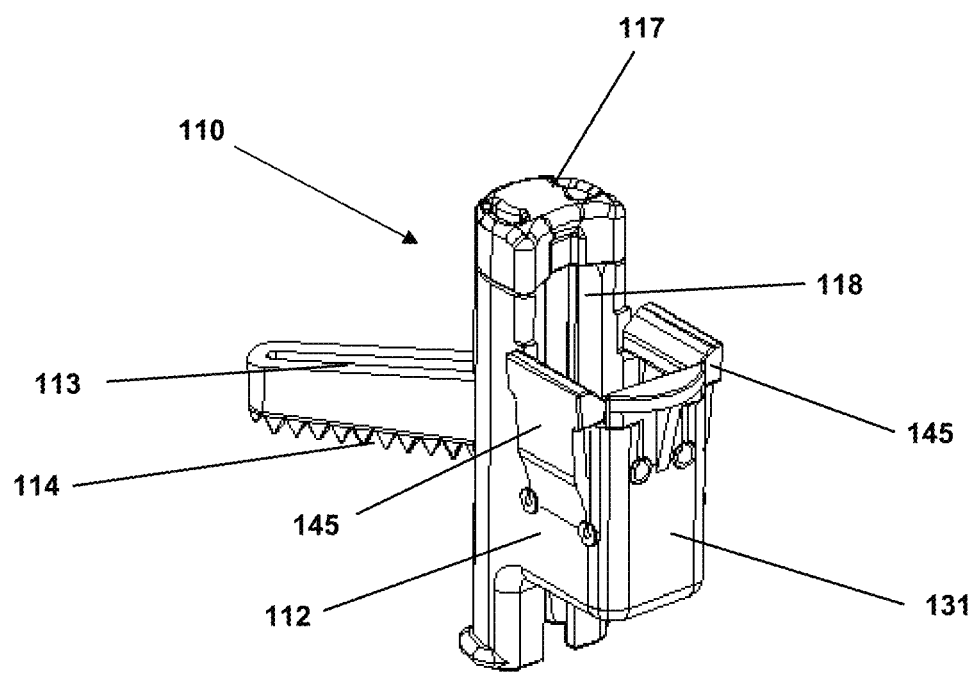
FIG. 14, is a view of the rear perspective of the carcass of the assembly shown in FIG. 12.

FIG. 14, is a perspective view of the rear plane of the frontal top assembly carcass 110 of the device 100, in which the top lid 117 stands out, the intermediate wall 118; the ends of the pressure release buttons 145; the rear wall 131 of the top carcass; the lateral wall 112: molded on the top carcass; the dented retention media 114, which have been molded on the top pressure paddle 113; the top pressure paddle 113, formed in one piece in the frontal top assembly carcass 110

The top frontal assembly carcass 110, includes a lid 117, molding the rear edge of the semi cylindrical frontal wall 111, to cover and form this way the assembly, whit a rounded corner to the front.

Figure 15:
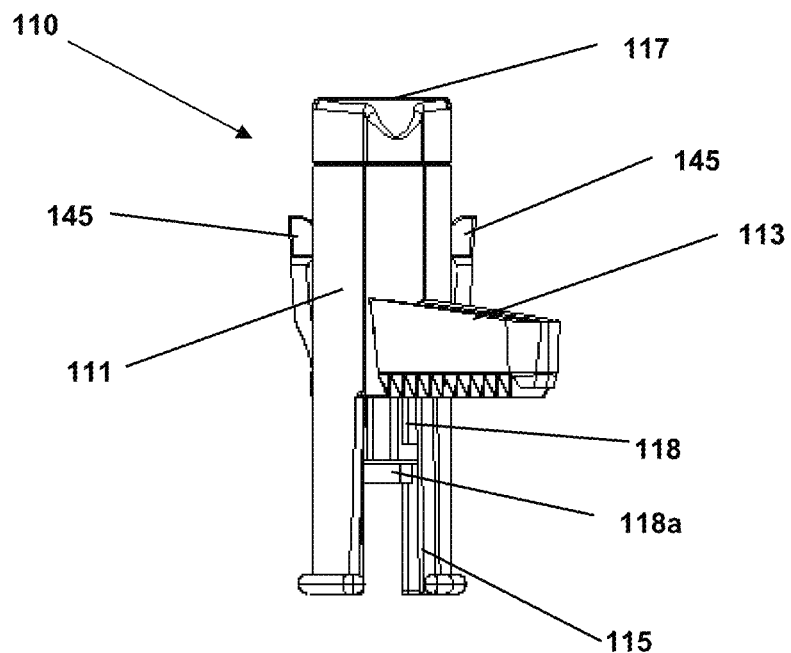
FIG. 15, is a view of the frontal plane of the carcass of the top assembly of the device shown in FIG. 12.

FIG. 15, is a view of the frontal plane of the top assembly carcass 110 of the device 100, where the top lid 117 can be seen; the ends of the pressure release buttons 145; the top pressure paddle 113, formed in one piece in the top frontal assembly carcass; the intermediate wall 118; the stair 118a, situated in the housing of the rear part of the carcass; the window 115, and; the semi cylindrical frontal wall 111, molded in the frontal part of the frontal top assembly carcass.

Figure 16:
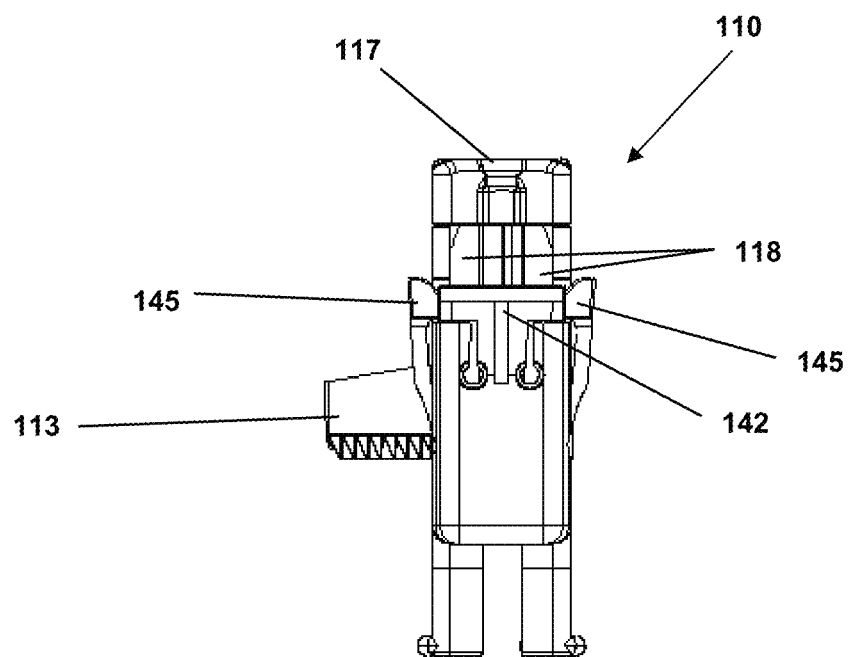
FIG. 16, is a view of the rear plane of the carcass of the top assembly of the device shown in FIG. 12.

FIG. 16, is a view of the rear plane of the top assembly carcass 110 of the device 100, where the top lid 117 can be seen; the intermediate wall 118; the ends of the pressure release buttons 145; the flexible elements 142 of the top carcass, and; the top pressure paddle 113, formed in one piece in the frontal top assembly carcass.

Figure 17:
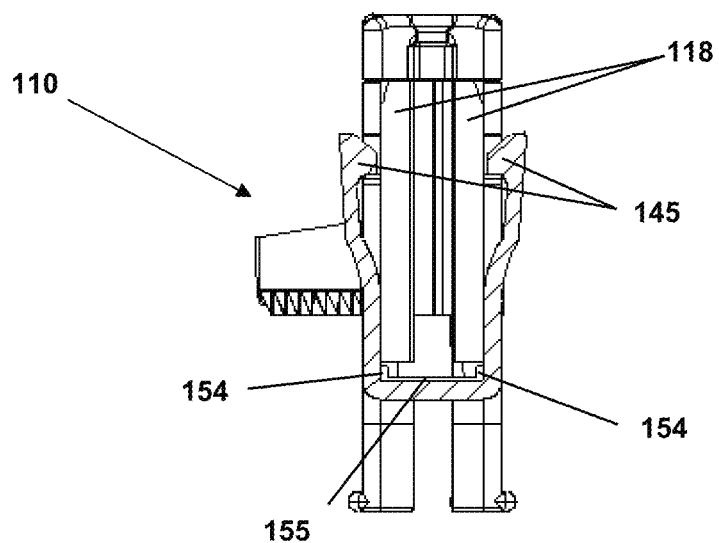
FIG. 17, is a cross-section view of the rear plane of the carcass of the top assembly of the device shown in FIG. 12.

FIG. 17, is a view of the cross-section of the rear plane of the top assembly carcass 110 of the device 100, where the intermediate wall can be seen; the ends of the pressure release buttons 145; the movement guides 154, and; the ramp 155.

Figure 18:
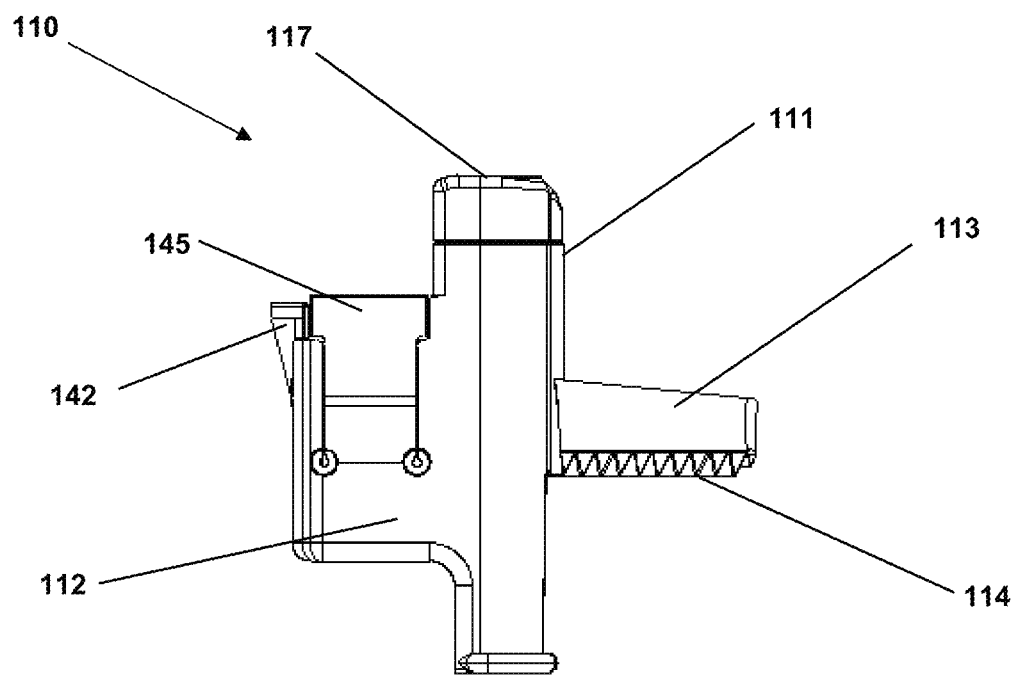
FIG. 18, is a left lateral view of the carcass of the top assembly shown in FIG. 12.

FIG. 18, is a left lateral view of the top assembly carcass 110 of the device 100, where the top lid 117 stands out, the top pressure paddle 113, formed in one piece in the frontal top assembly carcass; the dented retention media 114, which have been molded on the top pressure paddle 113; the lateral wall 112, molded on the top carcass; the flexible element 142 of the top carcass, and; one in of the pressure release buttons 145.

FIG. 19, is a left lateral view in cross-section of the top assembly carcass 110 of the device 100, in which can be seen the intermediate wall 118; the stair 118a situated in the housing of the rear part of the top carcass; the ramp 155; the movement guides 154; the flexible element 142 of the top carcass; and; one end of the pressure release buttons 145.

Figure 20:
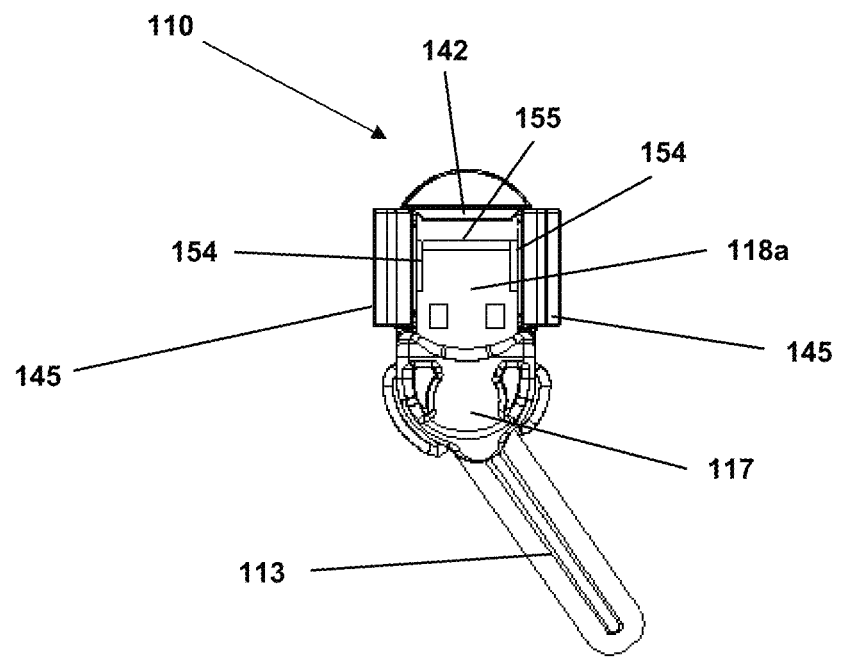
FIG. 20, is a view of the top plane the carcass of the top assembly shown in FIG. 12.

FIG. 20, is a view of the top plane of the top assembly carcass 110 of the device 100, where the flexible element 142 of the top carcass can be seen; the ramp 155; the movement guides 154; the stair 118a situated in the housing of the rear part of the carcass; the ends of the pressure release buttons 145; the top lid 117, and: the top pressure paddle 113.

Figure 21:
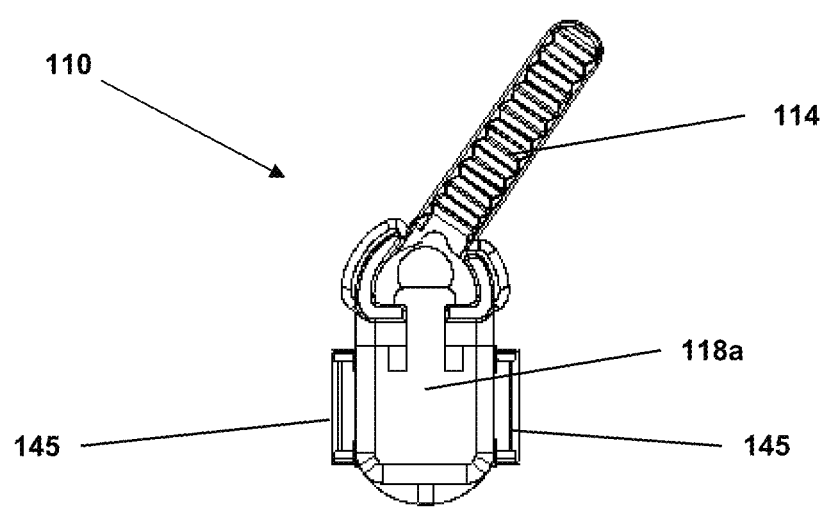
FIG. 21, is a view of the bottom plane of the carcass of the top assembly shown in FIG. 12.

FIG. 21, is a view of the bottom plane of the top assembly carcass 110 of the device 100, where the dented retention media 114 can be seen; the stair 118a situated in the housing of the rear part of the carcass, and; the ends of the pressure release buttons 145.

Figure 22:
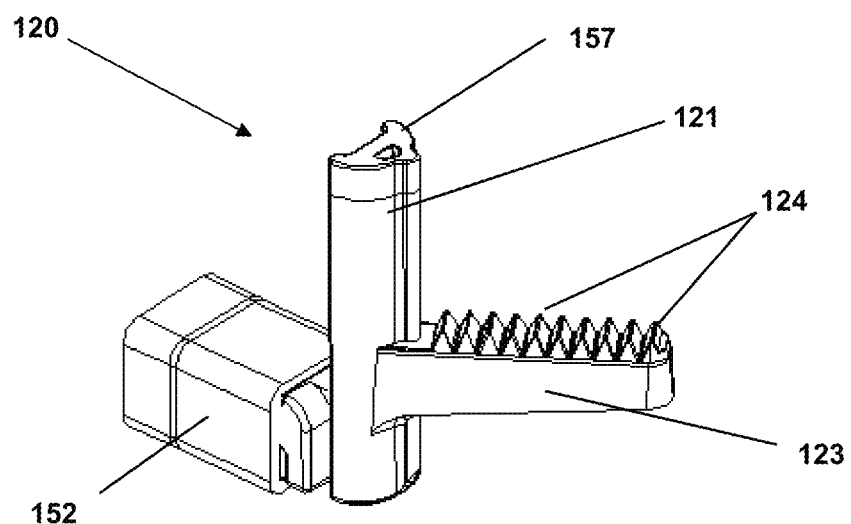
FIG. 22, is a view of the frontal perspective of the lower support assembly carcass of the device shown in FIG. 1.
Figure 28:
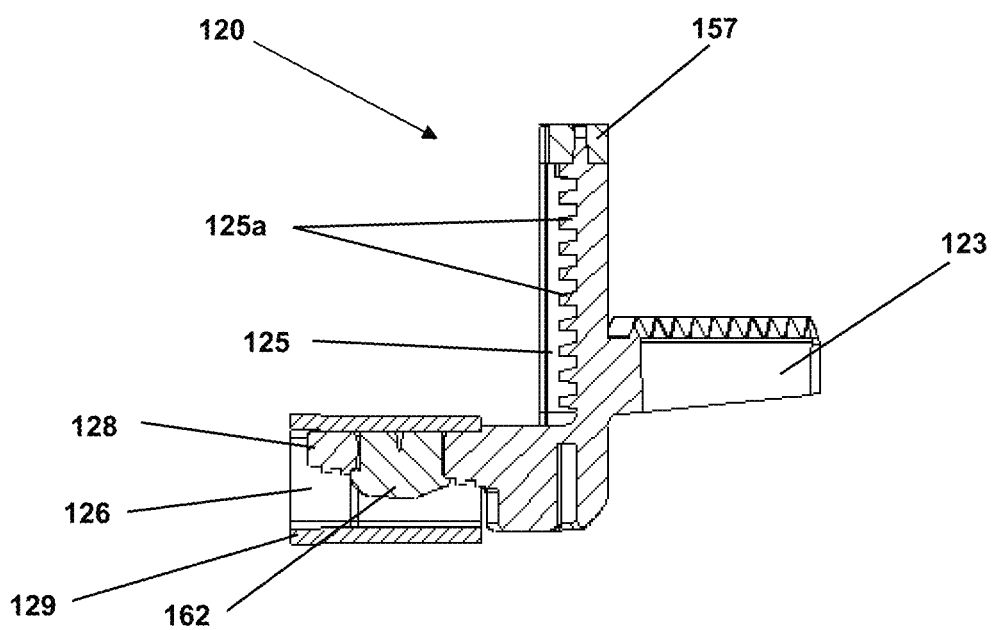
FIG. 28, is a left lateral view in cross-section of the assembly carcass of the lower support shown in FIG. 22.

The frontal carcass of the bottom assembly 120, which will be shown further on when describing FIGS. 22 and 28, includes a semi cylindrical frontal wall 121, and a bottom pressure paddle 123, which extends radially and at a 90° angle from the first lower third of the semi cylindrical front wall 121, which has been molded in one piece in the bottom front assembly carcass 120. Such bottom pressure paddle 123, includes a number of retention media 124, arranged on the top surface, uniformly distributed, which is a preferred modality of this invention, consist of superficial grooves (dented), that extend equidistant between them and on the whole top area of said pressure paddle 123.

FIG. 22, is a frontal perspective view of the lower support assembly carcass 120 of the device 100 with the top lid of the bottom carcass 157 can be seen; a frontal semi cylindrical wall 121, molded in the bottom support assembly carcass 120, the dented retention medias 124 of the interior pressure paddle 123 of the frontal carcass of the inferior ensemble 120, and the flexible grip piece 152.

Figure 23:
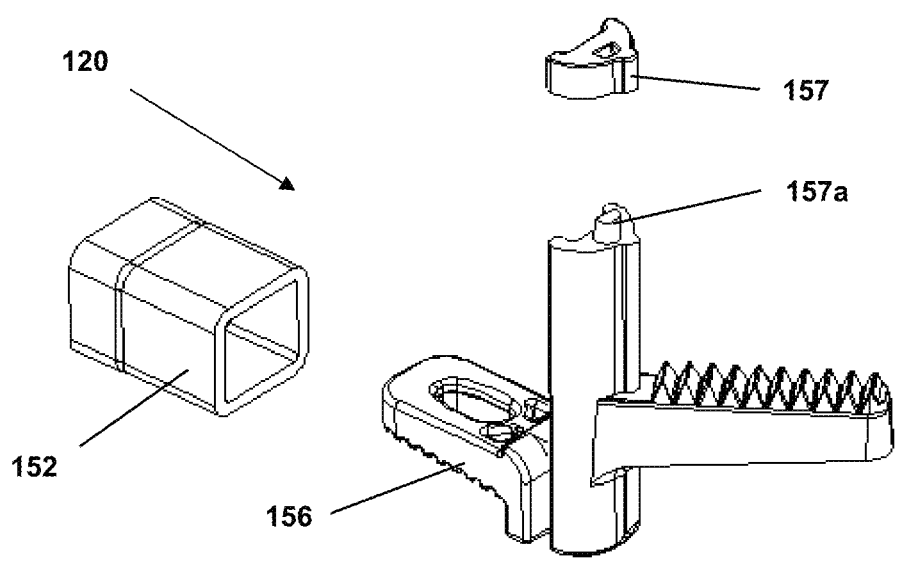
FIG. 23, is an exploded view of the frontal perspective of the lower support assembly carcass of the device shown in FIG. 1.

FIG. 23 is a perspective frontal exploded view of the lower support assembly carcass 120 of the device 100, where the lid of the bottom carcass 157 can be seen; the means of assembly by clamping 157a; the bottom carcass 156, and; the flexible grip part 152.

Figure 24:
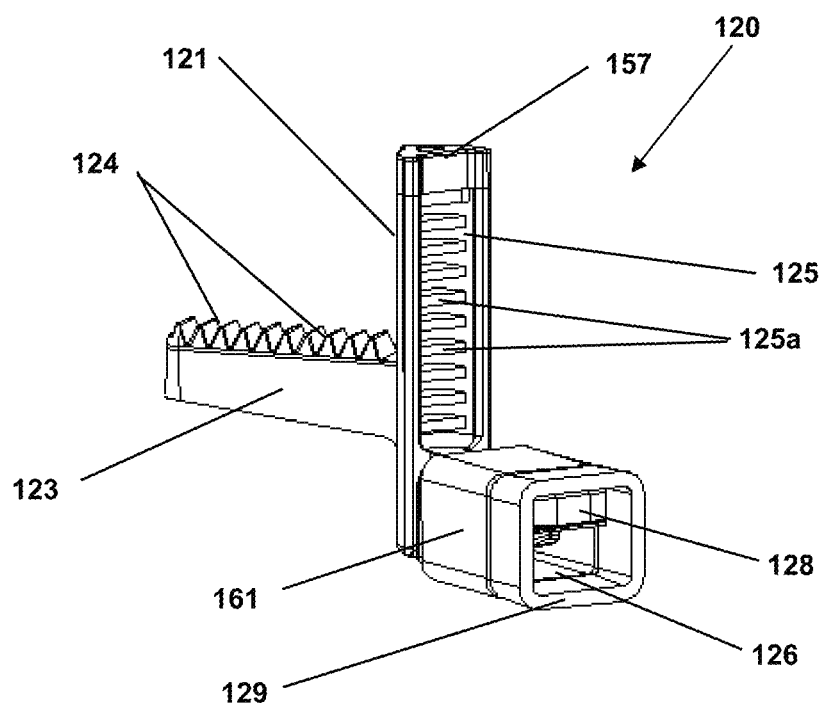
FIG. 24, is a perspective of the rear plane of the assembly carcass of the lower support shown in FIG. 22.

FIG. 24, is a perspective view of the rear plane of the lower support assembly carcass 120 of the device 100, where the bottom lid of the carcass can be seen 157; the channel 125; a number of dented grooves 125a; the crossbeam 128 formed on the posterior window 126; the edge of the base 129 molded on the flexible grip part 152 of the bottom assembly 120; the lateral wall 161 of the flexible grip part 152; the bottom pressure paddle 123; the dented retention media 124 of the bottom pressure paddle 123, and; the semi cylindrical frontal wall 121, molded on the lower support assembly carcass 120.

Figure 25:
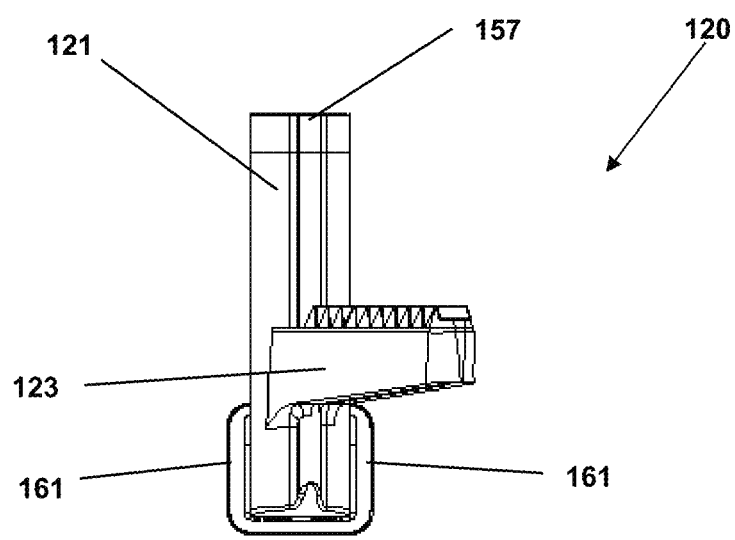
FIG. 25, is a frontal view of the assembly carcass of the lower support shown in FIG. 22.

FIG. 25 is a frontal view of the lower support assembly carcass 120 of the device 100, where the lid of the bottom carcass 157 can be seen; the lateral wall 161 of the flexible grip part 152; the bottom pressure paddle 123, and; the semi cylindrical frontal wall 121, molded in of the lower support assembly carcass 120.

Figure 26:
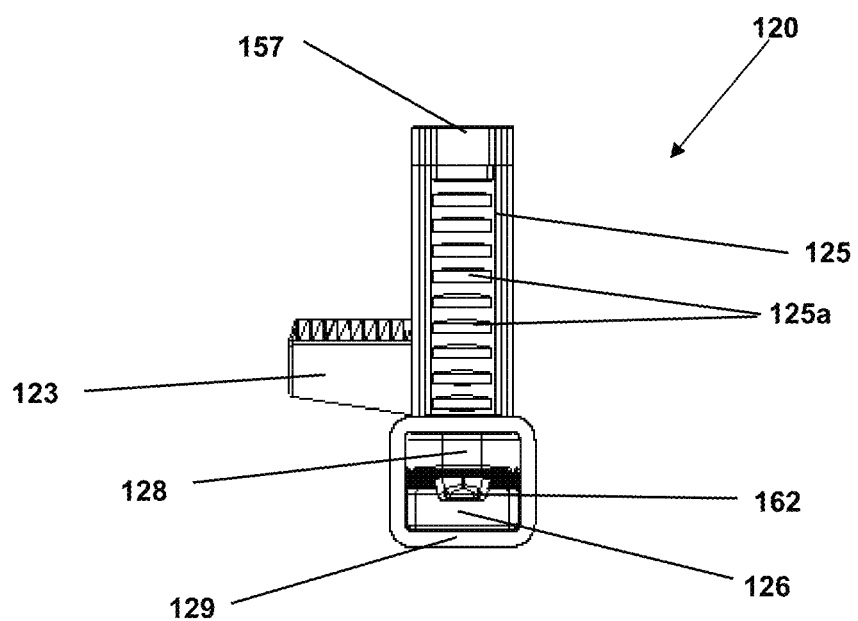
FIG. 26, is a rear view of the assembly carcass of the lower support shown in FIG. 22.

FIG. 26 is a rear view of the lower support assembly carcass 120 of the device 100, where the lid of the bottom carcass 157 can be seen; the channel 125; a number of dented grooves 125a; the pivot 162 of the flexible grip part 152; the edge of the base 129 molded on the flexible grip part 152 of the bottom assembly 120; the crossbeam 128 formed in the rear window 126, and; the bottom pressure paddle 123.

Figure 27:
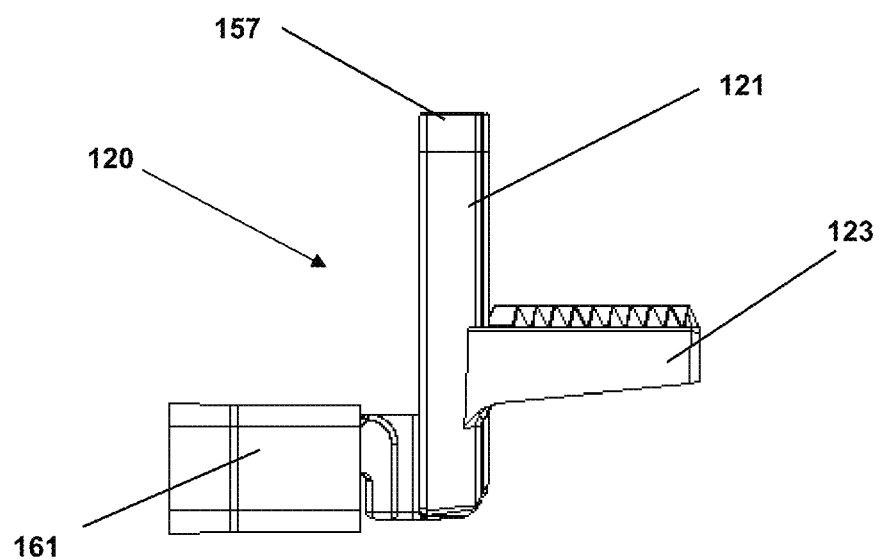
FIG. 27, is a left lateral view of the assembly carcass of the lower support shown in FIG. 22.

FIG. 27, is a left lateral view of the lower support assembly carcass 120 of the device 100, where the semi cylindrical frontal wall 121 can be seen, molded in of the lower support assembly carcass 120; the bottom pressure paddle 123, and; the lateral wall 161 of the flexible grip part 152.

FIG. 28 is a left lateral view in cross-section of the lower support assembly carcass 120 of the device 100, where the lid of the bottom carcass 157 can be seen; the bottom pressure paddle 123; the pivot 162 of the flexible grip part 152; the edge of the base 129 molded on the flexible grip part 152 of the bottom assembly 120; the rear window 126; the crossbeam 128 formed in the rear window 126; the channel 125, and; a number of dented grooves 125a.

Figure 29:
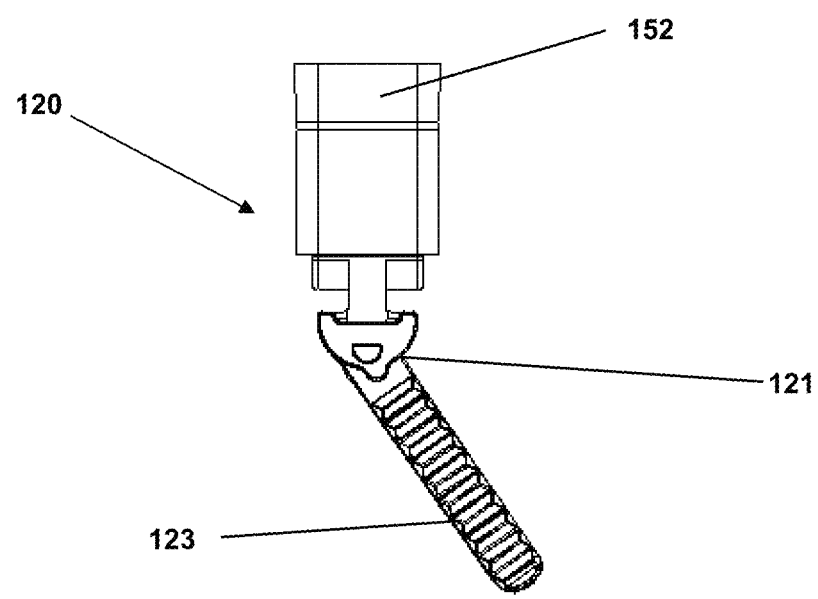
FIG. 29, is a view of the top plane of the assembly carcass of the lower support shown in FIG. 22.

FIG. 29, is a view of the top plane of the lower support assembly carcass 120 of the device 100, where the flexible grip part 152 can be seen 152; the semi cylindrical frontal wall 121, molded in the bottom carcass 120, and; the bottom pressure paddle 123.

In a particularly preferred modality of this invention, the bottom pressure paddle 123, shows an angle of approximately 55° towards the right in relation to the bottom frontal assembly carcass 120, taking into consideration the view of the frontal plane of the device 100.

Figure 30:
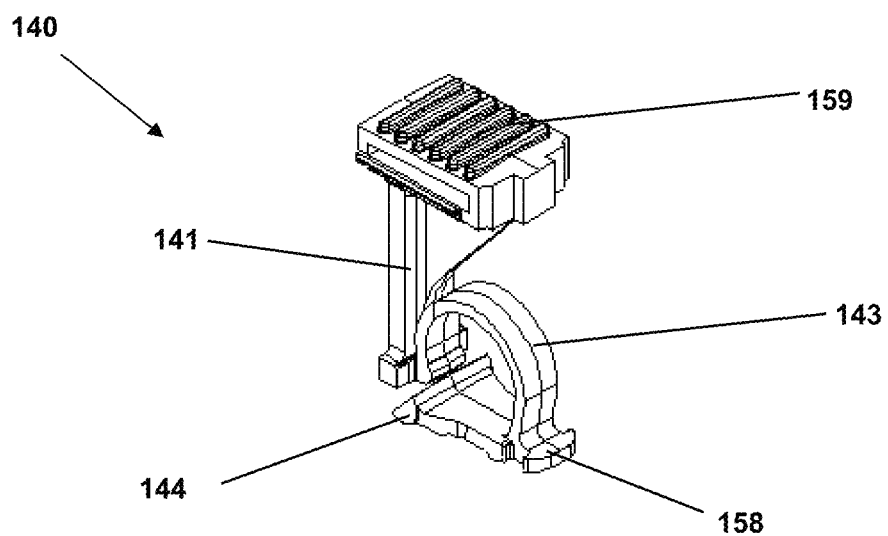
FIG. 30, is a frontal perspective view of the deformable element that is internally placed in the device shown in FIG. 1, and which has been constructed pursuant to the principles of a particularly preferred modality invention.

FIG. 30, is a frontal perspective of the deformable element 140, which is placed internally in the device shown in FIG. 1, and that has been built in accordance with the principles of a particularly preferred modality of this invention, where the top part 159 of the deformable element can be seen; the flexible guide 143 of the deformable element; the end 158 of the deformable element; the central extension 144 of the deformable element, and; the solid body 141 of the deformable element.

Figure 31:
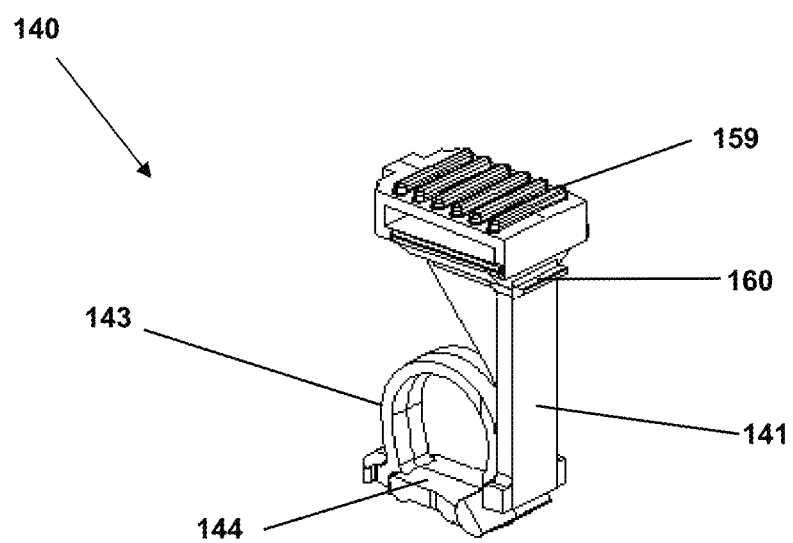
FIG. 31, is a perspective view of the rear plane of the deformable element shown in FIG. 30.

FIG. 31, is a perspective view of the rear plane of the deformable element 140 of the device 100, when the top part 159 of the deformable element can be seen; the support bump for anchoring 160 of the deformable element; the solid body 141 of the deformable element; the central extension 144 of the deformable element, and; the flexible guide 143 of the deformable element.

Figure 32:
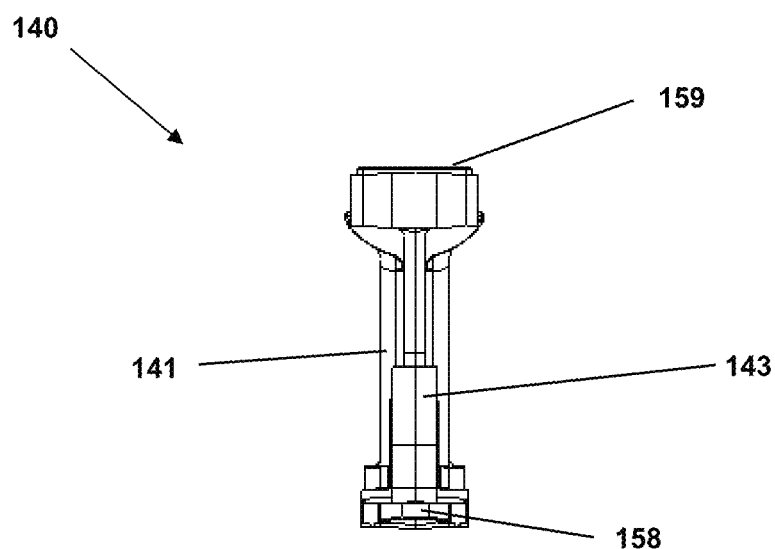
FIG. 32, is a view of the frontal plane of the deformable element shown in FIG. 30.

FIG. 32, is a view of the frontal plane of the deformable element 140 of the device 100, where the top part 159 of the deformable element can be seen; the flexible guide 143 of the deformable element; the end 158 of the deformable element, and; the solid body 141 of the deformable element.

Figure 33:
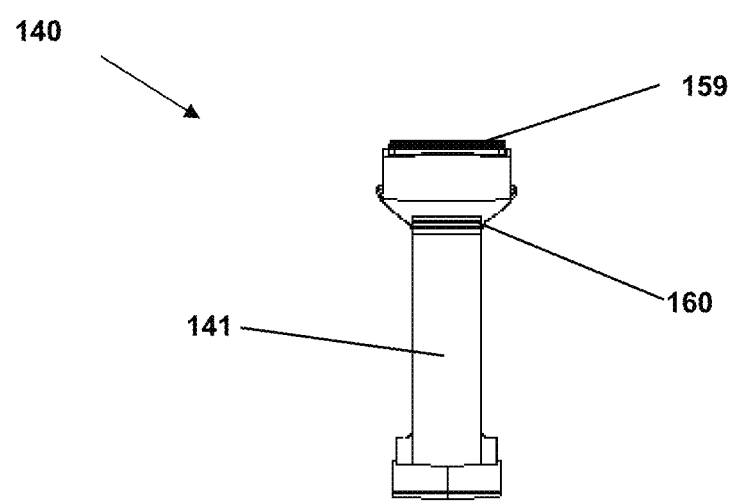
FIG. 33, is a view of the real plane of the deformable element shown in FIG. 30.

FIG. 33, is a rear plane view of the deformable element 140 of the device 100, where the top part 159 of the deformable element can be seen, the anchor boss 160, and; the solid body 141 of the deformable element.

Figure 34:
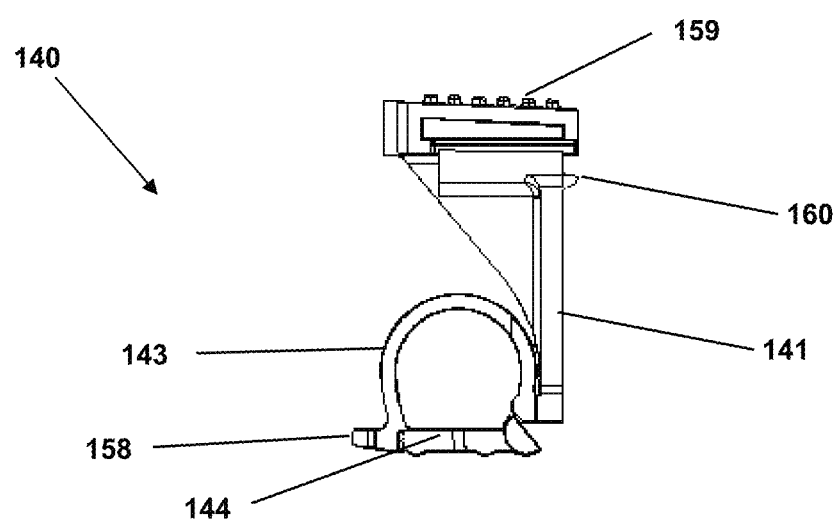
FIG. 34, is a right lateral view of the deformable element shown in FIG. 30.

FIG. 34, is a view of the right lateral plane of the deformable element 140 of the device 100, where the top part 159 of the deformable element can be seen, anchor boss 160; the solid body 141 of the deformable element; the central extension 144 of the deformable element; the end 158 of the deformable element, and; the flexible guides 143 of the deformable element.

Figure 35:
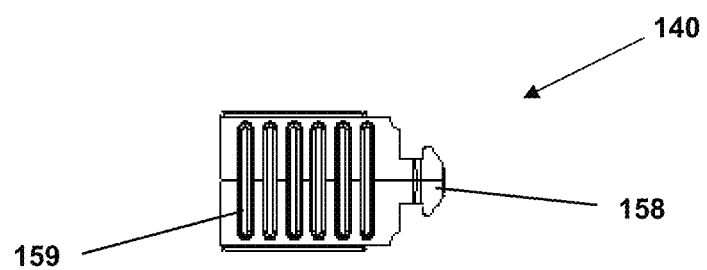
FIG. 35, is a view of the top plane of the deformable element shown in FIG. 30.

FIG. 35, is a view of the top plane of the deformable element 140 of the device 100, where the end 158 of the deformable element can be seen, and; the top part 159 of the deformable element.

Figure 36:
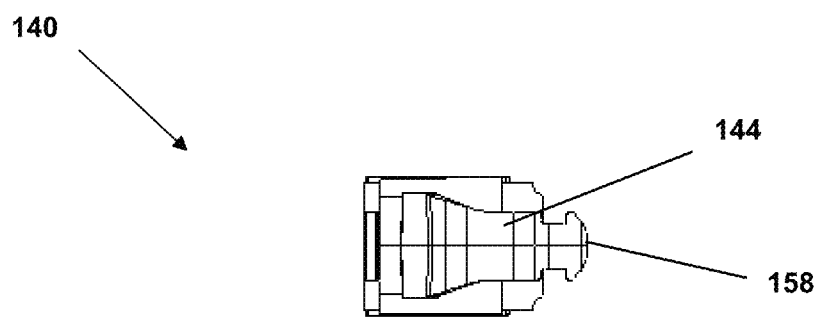
FIG. 36, is a view of the top plane of the deformable element shown in FIG. 30.

FIG. 36, is a view of the bottom plane of the deformable element 140 of the device 100, where the central extension 144 of the deformable element; and; the end 158 of the deformable element can be seen.

Figure 37:
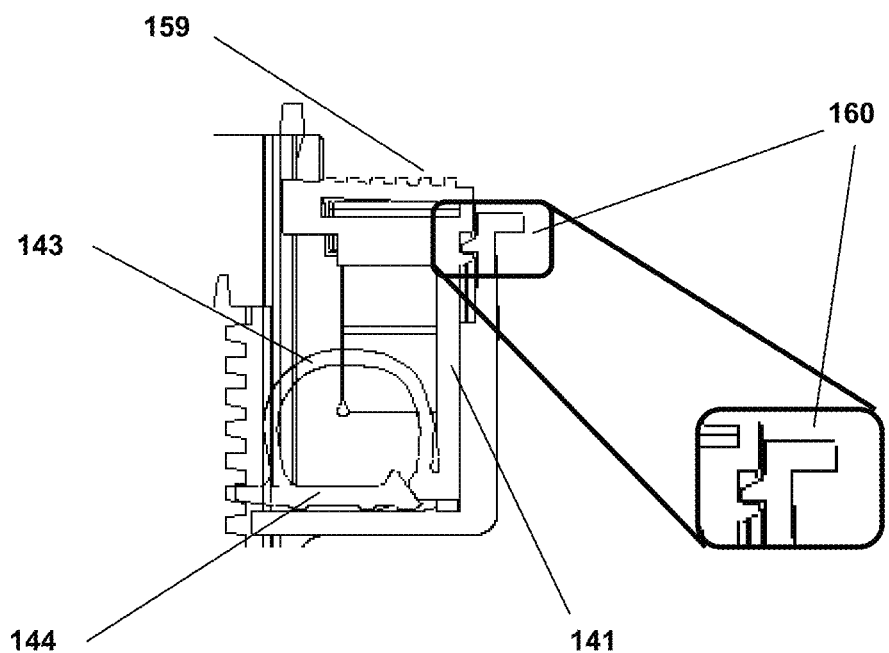
FIG. 37, is a cross-section view of the detail of the locking mechanism of the deformable element of the invention device.

FIG. 37, is a cross-section view of the detail of the locking mechanism of the deformable element 140 of the device 100, where the top part 159 of the deformable element; the detail of the support bump for anchoring 160 in a closed position; the solid body 141 of the deformable element; the central extension 144 of the deformable element, and; the flexible guide 143 of the deformable element can be seen.

Figure 38:
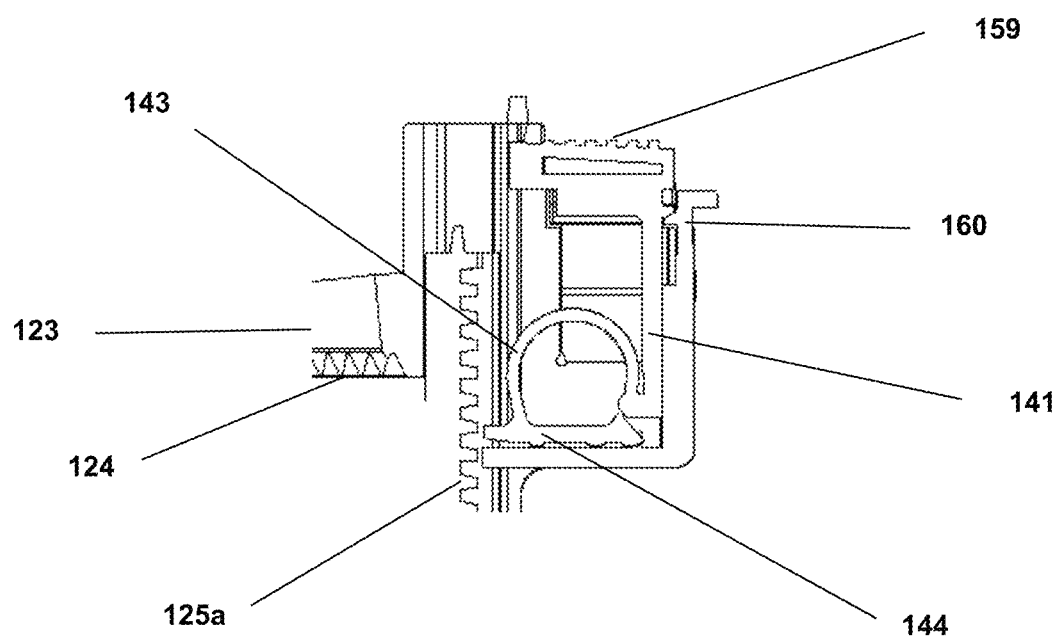
FIG. 38, is a cross-section view of the detail of the locking mechanism of the deformable element in an open position of the invention device.

FIG. 38, is a cross-section view of the detail of the locking mechanism of the deformable element 140 of the device 100, with the top part 159 of the deformable element; the detail of the support bump for anchoring 160 in an open position; the solid body 141 of the deformable element; the central extension 144 of the deformable element; a number of dented grooves 125a; the retention dented media 124 of the bottom pressure paddle 123; the bottom pressure paddle 123, and; the flexible guide 143 of the deformable element can be seen.

Figure 39:
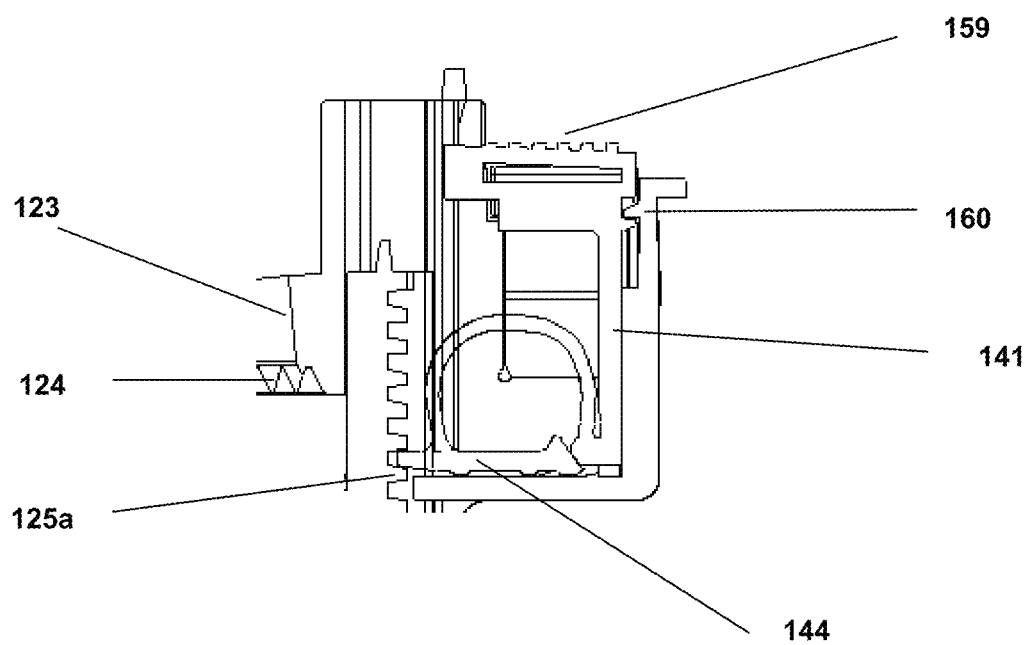
FIG. 39, is a cross-section view of the detail of the unlocking mechanism of the deformable element in closed position of the invention device.

FIG. 39, is a cross-section view of the detail of the locking mechanism of the deformable element 140 of the device 100, where the top part 159 of the deformable element; the detail of the support bump for anchoring 160 in a closed position; they solid body 141 of the deformable element; the central extension 144 of the deformable element; a number of dented grooves 125a; the dented retention media 124 of the bottom pressure paddle 123; bottom pressure paddle 123, and; the flexible guide 143 of the deformable element can be seen.

Figure 40:
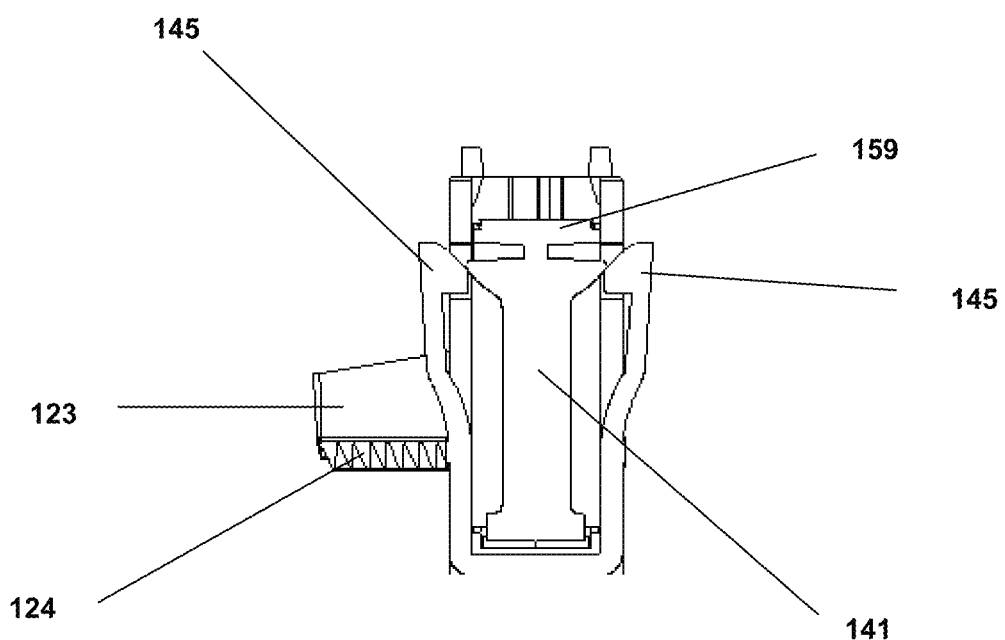
FIG. 40, is a cross-section view of the detail of the rear plane of the unlocking mechanism of the deformable element of the invention device.

FIG. 40, is a cross-section view of the detail of the rear plane of the unlocking mechanism update deformable element 140 of the device 100, where the top part 159 of the deformable element; and of the pressure release buttons 145; the solid body 141 of the deformable element, and; the retention media 124 of the bottom pressure paddle 123 can be seen.

As can be observed in the figures of the device for occlusion of blood vessels 100 of this invention, the top frontal assembly carcass 110, receives on its bottom end, the top end of the bottom assembly frontal carcass 120; the semi cylindrical front wall 121, it slides inside the cavity that is formed by the rear surface of the semi cylindrical front the wall 111 and the intermediate wall 118, inserting the elastic media 150 between both, the top and bottom carcasses, to exercise pressure.

In the spaces formed by the intermediate wall 118, are included media that receive channel 125 of the support assembly 120 coupling to serve as guides for sliding between the top assembly 110 and the support assembly 120.

The deformable element 140, slides to into the top frontal assembly carcass 110, to be deposited on the step 118a, located in the housing of the rear part of the top frontal assembly carcass 110, formed by the rear face of the semi cylindrical front wall 111, placing the top lid 117 through the adequate clamping media. The ends of the buttons 145, are exposed and outside for handling on the sides of the device.

In accordance with the foregoing, the deformable element 140 is designed in a shape and material such that it limits the force exerted by pressing said deformable element 140 at the time of closing the device for occlusion of blood vessels 100.

In the preferred modality of this invention, has with elastic media 150, preferably springs, that have a function of preventing, the inappropriate occlusion of device 100 and, its quick opening of the same when the pressure release buttons 145.

In other modalities, elastic media could be dispensed with, which does not affect the scope of the invention, since the lack of elastic media, as a consequence, makes the release of the device less effective than it is in the preferred modality.

Once the top frontal assembly carcass 110, the bottom frontal assembly carcass 120, the deformable element 140 and the elastic media 150 are all coupled, the assembly of device 100 is complete, assembling the flexible grip part 152, which allows the application of one of the jaws of the Foerster Clamps, having access to the deformable element 140.

This way, the assembly carcasses 110 and 120, with their respective pressure paddles 113 and 123, slide vertically to occlude or liberate an artery.

As can be seen in the enclosed figures, the window 115 of the top frontal assembly carcass 110, allows the reception and coupling of the pressure paddle 123 when it slides vertically upwards and the intermediate wall 118, prevents horizontal displacement of such pressure paddle 123, thus complying in a more efficient way the occlusion functioning.

As mentioned, with the coupling of the top assembly carcasses 110 and the modern assembly 120, the channel 125 receives the end 158 of the deformable element 140, lying such end 158 perpendicularly placed with regards to the axis of the channel 125. The end 158, together with the deformable element 142, has the function of stops to limit the force exercised on the deformable element 140. When the pre-established force is overcome, when the end 158 is displaced and are secured with a number of dented grooves 125a that are present all along the length of channel 125, the displacement vertical movement of device 100 is limited, securing this way, the occlusion of the artery, without overdoing the required force to that effect.

In order to operate the device with Foerster Clamps, is placed on the top part 159 of the deformable element 140, to be able to exert correct pressure. On each of the distal ends of the top part 159, a button 145 is placed exposed on the sides of the device; such buttons 145, when pressed simultaneously, after the device has been in a closed position and occluding, release the pressure paddles 113 and 123, to allow the withdrawal of the device 100.

The pressure paddles 113 and 123, include an angular profile simulating the configuration of the Foerster Clamps. The dented retention media 114 and 124, on the contact surfaces of the pressure paddles 113 and 123, allow securing the tissue of the artery without damaging it at the exact efficient pressure for occlusion, nor the tissue surrounding them, as opposed to what happens when using Foerster Clamps to occlude cesarean or postpartum resulting hemorrhages.

The operate of the device 100, the top part 159 of the deformable element 140 is pressed until the support bump for anchoring 160 is coupled in its place; when pressed it deforms the deformable body 140, and sliding its horizontal end 158, which is inserted in the groove zone formed by the number of dented grooves 125a.

In order to unlock, the pressure release buttons 145, are pushed simultaneously, which sliding towards the center, cause the release button bumps 145, push upwards, allowing them to return to their original position, liberating this way, the anchoring of the flexible element 142, unlocking the device, thus allowing the withdrawal from the patient's body.

Without intending to limit the reach of this invention which reveals itself in terms of this document, which is presented only with illustrative purposes, although not limited, to allow the full comprehension of the modalities of this invention, without implying that there are no other modalities that can be configured for other uses according to their revealed principles in terms of this invention, and therefore, can be put into practice-based on the detailed description of the preferred modality of this invention, in the specific case of hemorrhages resulting from cesarean or postpartum, the device of this invention, turns out to be especially practical, since it's not only performs efficiently in his function to occlude veins and/or arteries for the control of hemorrhages, but it also allows to control the force with which the affected blood vessel is occluded, achieving such purpose without hurting the tissue of the occluded zone. The latter is due to the presence of the deformable element which causes the occluding force applied to be always the same, regardless of the force applied press the device, since generally, the force applied to the tissue is not controlled or limited, which, in the majority of cases, is not ideal to occlude the blood vessel in question, since due to the inappropriate pressure being applied, it could hurt or affect the tissue of the occluded zone, increasing the risks of tissue hypoxia and/or necrosis, just like in normal practice happens when using Foerster Clamps to occlude cesarean or postpartum resulting hemorrhages.

The Forrester clamp consists of a long curved or straight clamp which features a rack of considerable length that allows the pressure on the tip to be adjusted at will; each jaw of the Foerster clamp ends in a grooveless loop with an opening that allow the occlusion of preferably hollow tissue, which has the disadvantage of impeding the control of force with which it is applied, which in some cases affects the tissue around the area that is being occluded, therefore increasing the risk of tissue hypoxia and/or necrosis Due to the angle of approximately 55° towards the right which the pressure paddles 113 and 123 show with reference to the front carcass of the top assembly 110 and the front carcass of the bottom assembly 120 of this invention's device, it facilitates and makes more efficient the placement of the device on the blood vessels, on both the right and the left side of the anatomy of the patient.

Placement Method

Having described this invention's device, following is the description of the method of preferred use for the obstruction of the uterine arteries via the vaginal.

The method for placement of this invention's device, besides using this invention the device, ideally requires the following medical instruments:

Two of this invention's devices (henceforth "Life Clip")
Two straight ring clamps
Two curved ring clamps
One Foley or Nelaton catheter
Two Eastman valves, or one vaginal mirror, should valves not be available The placement of this invention's device described below, is used to block the uterine arteries via the vaginal:

i) The patient in the lithotomy position
ii) Transuterine catheter placement and bladder emptying
iii) A first life clip is articulated on the curved ring clamp, leaving it ready for placement. The one being applied to the left side of the patient, is articulated on the clamp, with the top assembly 110 facing up;
iv) The second life clip is articulated on the curved ring clamp, leaving it ready for placement. The one being applied to the right side of the patient, is articulated on the clamp, with the top assembly 110 facing down;
v) The assistant places the anterior valve and the posterior valve into the vagina, in order to visualize the cervix;
vi) Clamp is applied to the central part of the anterior lip of the uterine cavity with a curved ring clamp and afterwards, the central part of the posterior lip with the other curved ring clamp.
vii) Anterior and posterior valves are then moved towards the left side of the vagina, with a soft traction movement of the ring clamps outwards and to the right of the patient.
viii) The left cardinal ligament is palpated between the middle and index fingers of the right hand, in order to obtain an anatomical point of reference.
ix) Life Clip, articulated to the curved ring clamp is introduced, making sure that the compression zone is in a medial-distal direction, 2 cm away from the cardinal ligament;
x) Once it is confirmed that the entire thickness of the cervix is inside the area of compression, then Life Clip is closed, making sure it has been securely fastened;
xi) The valves are then moved towards the right side of the patient, with a soft traction movement of the straight ring clamps, outwards and to the left;
xii) The cardinal right ligament is palpated, between the middle and index fingers of the left hand, in order to obtain an anatomical point of reference;
xiii) Life Clip, articulated to the curved ring clamp is introduced, making sure that the compression zone is in a medial-distal direction, 2 cm away from the cardinal ligament:
xiv) Once it is confirmed that the entire thickness of the cervix is inside the area of compression, then Life Clip is closed, making sure it has been securely fastened;
xv) Once both Life Clips have been placed, corroboration is made that there is permeability of the cervix by passing the curved ring clamp;
xvi) Removal of both straight ring clamps.
xvii) Immediate corroboration that the loss of blood has considerably diminished.

The method for the removal of this invention's device, ideally must be carried out in a hospital, having all the installed infrastructure, in case that medical or surgical abdominal intervention is needed by trained medical personnel to carry out such interventions.

To that effect, Life Clips must be available in case it is decided to place new ones.

In a first case scenario, once the cause of obstetric hemorrhage has been identified and resolved, and the patient is hemodynamically stable, the following actions take place:

i) Patient in lithotomy position;
ii) Bladder emptying corroboration;
iii) the assistant places the anterior and posterior valves in the vagina in order to visualize the cervix and the Life Clips;
iv) With the curved ring clamp, the lock is deactivated liberating the Life Clip in question and it is removed from the vagina. The same procedure is applied to remove the counter lateral Life Clip.

In a second case scenario, where the hemorrhage has not been solved, for instance in the case of Uterine Atony, the patient continues with laparotomy, following the same removal procedure, until the cause of bleeding has been resolved, or in case it is required during hysterectomy, at the moment uterine arteries are reached via the abdomen.

As a result of the description of the occluding device and its usefulness, it must be obvious for a technician with knowledge of the subject, that the occlusion of uterine arteries is just an example of the multiple applications or uses that this device offers, since in general it can be used for occluding veins, arteries or other conduits.

It will be evident that for experts on the subject, the assembly of the device can be done through other means like pivots and/or adhesives, without the latter meaning that, when describing the modalities of this invention, it is intended to limit the scope of the invention presented on this document.

What is claimed is:

1. A device for occlusion of blood vessels and hemorrhage control, the device comprising:
   a) an upper housing with an open bottom end, the upper housing comprising:
      a top chamber having an upper front wall at a front of the top chamber and an intermediate wall at a rear of the top chamber, the upper front wall having a front window extending from the open bottom end upwards;
      an upper cap closing a top of the top chamber;
      a top pressure paddle extending frontward from the upper front wall above the front window;
      a rear basket extending rearward behind the intermediate wall, the rear basket having a floor, a rear wall, and lateral walls;
      wherein a slot opens on the intermediate wall, above the floor;
   b) a lower housing, comprising:
      a bottom chamber partially enclosing a channel and having a bottom front wall, the bottom chamber being open on a rear section thereof and having a plurality of spaced-apart horizontal projections extending inside the channel;
      a bottom pressure paddle extending frontward from the bottom front wall;
      a bottom cap closing a top of the bottom chamber;
      wherein the bottom chamber is shaped to fit inside the top chamber such that the bottom pressure paddle extends forward through the front window when the bottom chamber is placed inside the top chamber;
      wherein the bottom chamber is configured to slide vertically along the top chamber, to occlude a blood vessel by pressing the blood vessel between the top pressure paddle and the bottom pressure paddle;
   c) a compressible elastic medium located within the top chamber of the upper housing, between the bottom cap of the lower housing and the upper cap;
   d) a deformable element comprising a top part, a flexible guide, and a forward end, the deformable element being located inside the rear basket, such that the forward end is aligned with the slot on the intermediate wall;
      wherein downward pressure on the top part causes a deformation of the flexible guide, which in turn causes the forward end to slide though the slot inside the channel of the bottom chamber which is located inside the top chamber, and into a space between any two successive horizontal projections, to maintain the bottom chamber at a desired location within the top chamber, thereby maintaining a desired distance between the top pressure paddle and the bottom pressure paddle, to control pressure on the blood vessel pressed between the top pressure paddle and the bottom pressure paddle;
   e) an anchoring mechanism configured to anchor the deformable element and maintain the deformation of the flexible guide and an extension of the forward end without continued application of pressure on the top part; and
   f) a release mechanism configured to be manipulated to release anchoring of the deformable element, thereby causing the flexible guide to return to an original shape thereof, thereby retracting the forward end away from the plurality of spaced-apart horizontal projections.

2. The device of claim 1, wherein the anchoring mechanism comprises:
   an inner jutting extending into the rear basket;
   a support bump located below the top part, creating a groove between the support bump and the top part;
   wherein the inner jutting is configured to cooperate with the groove when the top part is pushed downwards, thereby maintaining the deformation of the flexible guide and the extension of the forward end without continued application of pressure on the top part.

3. The device of claim 2, wherein the release mechanism comprises at least one pressure release button on the rear basket, such that when the at least one pressure release button is pressed, the at least one pressure release button is configured to disengage the groove from the inner jutting, such that the flexible guide returns to the original shape thereof and the forward end retracts.

4. The device of claim 2, wherein the release mechanism comprises two pressure release buttons located at respective lateral walls of the rear basket, such that when both pressure release buttons are pressed, the two pressure release buttons are configured to apply an upward force to the deformable element, thereby disengaging the groove from the inner jutting, such that the flexible guide returns to the original shape thereof and the forward end retracts.

5. The device of claim 1, wherein the upper front wall is semi-cylindrical.

6. The device of claim 1, wherein the bottom front wall is semi-cylindrical.

7. The device of claim 1, wherein:
   the top pressure paddle comprises retention media distributed along a lower surface thereof, forming a plurality of first grooves;
   the bottom pressure paddle comprises retention media distributed along an upper surface thereof, forming a plurality of second grooves.

8. The device of claim 1, wherein the lower housing comprises a cross beam extending rearward from a bottom of the lower housing.

9. The device of claim 8, comprising a flexible sheath joined to the cross beam.

10. The device of claim 1, wherein the deformable element further comprises a solid body joining the top part to the flexible guide.

11. The device of claim 10, wherein the flexible guide is curved, and has a first end joined to the solid body and a second end joined to a central extension extending on the floor, the central extension ending with the forward end;

such that when the top part is pressed, the solid body is configured to travel downward, deform the flexible guide and contact a rear end of the central extension, causing the central extension to move forward, thereby sliding the extension of the forward end into the space between two successive spaced-apart horizontal projections.

* * * * *